(12) United States Patent
Charest et al.

(10) Patent No.: US 11,006,977 B2
(45) Date of Patent: May 18, 2021

(54) GROWING ROD FOR TREATING SPINAL DEFORMITIES AND METHOD FOR USING SAME

(71) Applicant: GLOBUS MEDICAL, INC., Audubon, PA (US)

(72) Inventors: Joshua Charest, Philadelphia, PA (US); Derrick Bingaman, Collegeville, PA (US); Bobby Lynch, Gainesville, FL (US)

(73) Assignee: Global Medical Inc, Audubon, PA (US)

( * ) Notice: Subject to any disclaimer, the term of this patent is extended or adjusted under 35 U.S.C. 154(b) by 36 days.

(21) Appl. No.: 15/947,908

(22) Filed: Apr. 9, 2018

(65) Prior Publication Data
US 2018/0221061 A1    Aug. 9, 2018

Related U.S. Application Data

(63) Continuation-in-part of application No. 15/243,218, filed on Aug. 22, 2016, now Pat. No. 10,226,281, which is a continuation-in-part of application No. 14/874,771, filed on Oct. 5, 2015, now Pat. No. 9,949,759.

(51) Int. Cl.
*A61B 17/70*    (2006.01)

(52) U.S. Cl.
CPC ........ *A61B 17/7014* (2013.01); *A61B 17/702* (2013.01); *A61B 17/7016* (2013.01); *A61B 17/7017* (2013.01); *A61B 17/7025* (2013.01)

(58) Field of Classification Search
CPC ............ A61B 17/7014; A61B 17/7016; A61B 17/7017; A61B 17/702; A61B 17/7025
See application file for complete search history.

(56) References Cited

U.S. PATENT DOCUMENTS

| | | |
|---|---|---|
| 458,984 A | 9/1891 | Smith |
| 1,245,921 A | 11/1917 | Holdren |
| 1,404,816 A | 1/1922 | Wegstein |
| 1,698,618 A | 1/1929 | Bigelow |
| 1,852,776 A | 4/1932 | Hodeaux |
| 2,231,427 A | 2/1941 | Larsh et al. |
| 2,441,846 A | 5/1948 | Schaaff et al. |
| 2,578,279 A | 12/1951 | Bardwell |
| 3,430,510 A | 3/1969 | Hendrickson |
| 3,461,738 A | 8/1969 | Pandjiris et al. |
| 3,535,948 A | 10/1970 | Winzeler et al. |
| 3,710,640 A | 1/1973 | Stranger et al. |
| 4,077,274 A | 3/1978 | Johnson |
| 4,215,599 A | 8/1980 | Batchelder et al. |

(Continued)

FOREIGN PATENT DOCUMENTS

| | | |
|---|---|---|
| JP | 2009511101 A | 3/2009 |
| JP | 2015519972 A | 7/2015 |
| WO | 2014145470 A2 | 9/2014 |

*Primary Examiner* — Julianna N Harvey

(57) ABSTRACT

An implantable growing rod assembly adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis.

20 Claims, 27 Drawing Sheets

(56) References Cited

U.S. PATENT DOCUMENTS

| | | |
|---|---|---|
| 5,345,845 A | 9/1994 | Myers |
| 5,630,343 A | 5/1997 | Begin |
| 5,700,263 A | 12/1997 | Schendel |
| 5,934,144 A | 8/1999 | Marinkovic |
| 7,029,472 B1 | 4/2006 | Fortin |
| 7,979,988 B2 | 7/2011 | Shiino et al. |
| 8,113,074 B2 | 2/2012 | Wohrle et al. |
| 8,137,349 B2 * | 3/2012 | Soubeiran .......... A61B 17/7216 606/63 |
| 8,568,457 B2 * | 10/2013 | Hunziker .......... A61B 17/7016 606/246 |
| 8,591,547 B2 | 11/2013 | Swisson, III et al. |
| 8,641,723 B2 | 2/2014 | Connor |
| 9,301,788 B2 | 4/2016 | Wolters et al. |
| 9,561,061 B2 | 2/2017 | Swisson, III et al. |
| 9,707,096 B2 * | 7/2017 | Sutterlin, III ......... A61F 2/4611 |
| 9,931,138 B2 * | 4/2018 | Lynch ................ A61B 17/7025 |
| 10,092,328 B2 * | 10/2018 | Sharifi-Mehr ..... A61B 17/7011 |
| 10,226,281 B2 * | 3/2019 | Lynch ................ A61B 17/7014 |
| 2004/0206195 A1 | 10/2004 | Landskron et al. |
| 2006/0122606 A1 | 6/2006 | Wolgen |
| 2006/0195088 A1 | 8/2006 | Sadler et al. |
| 2010/0004697 A1 | 1/2010 | Fortin et al. |
| 2010/0094302 A1 * | 4/2010 | Pool .................... A61B 17/7079 606/90 |
| 2011/0137347 A1 * | 6/2011 | Hunziker .......... A61B 17/7016 606/258 |
| 2013/0338713 A1 * | 12/2013 | Kawakami ........ A61B 17/7014 606/258 |
| 2014/0074168 A1 * | 3/2014 | Mundis .............. A61B 17/7025 606/260 |
| 2014/0155946 A1 * | 6/2014 | Skinlo ................ A61B 17/8872 606/86 R |
| 2014/0250674 A1 * | 9/2014 | Pool ...................... A61B 17/68 29/525.11 |
| 2014/0276822 A1 | 9/2014 | Cresina et al. |
| 2016/0199101 A1 * | 7/2016 | Sharifi-Mehr ..... A61B 17/7017 606/258 |
| 2016/0324550 A1 | 11/2016 | Wolters et al. |
| 2017/0095275 A1 * | 4/2017 | Lynch ................ A61B 17/7014 |
| 2017/0150975 A1 * | 6/2017 | Bozung ............. A61B 17/1626 |
| 2017/0325854 A1 | 11/2017 | Rouge |
| 2018/0028239 A1 | 2/2018 | Swisson, III et al. |
| 2018/0110543 A1 * | 4/2018 | Ingalhalikar ....... A61B 17/7025 |
| 2018/0221061 A1 * | 8/2018 | Charest ............. A61B 17/7014 |
| 2019/0209211 A1 * | 7/2019 | Charest ............. A61B 17/7014 |

* cited by examiner

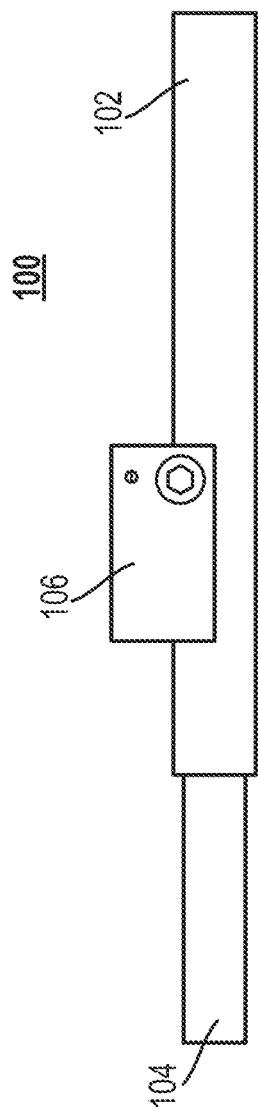
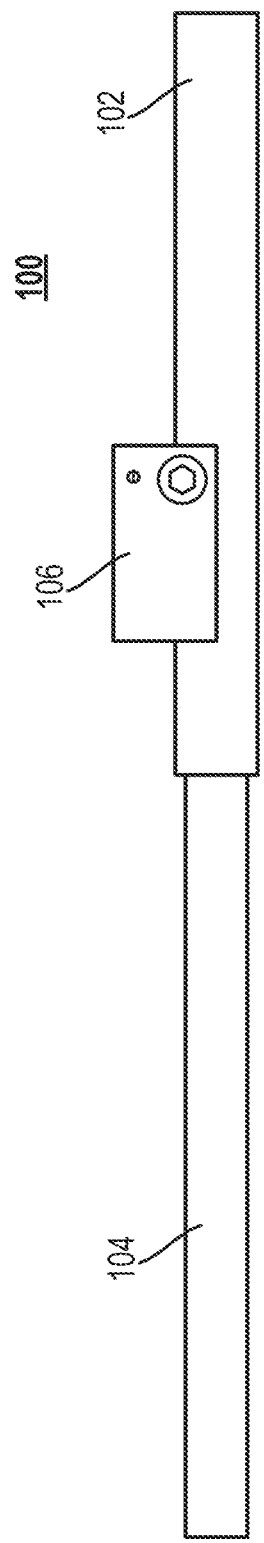

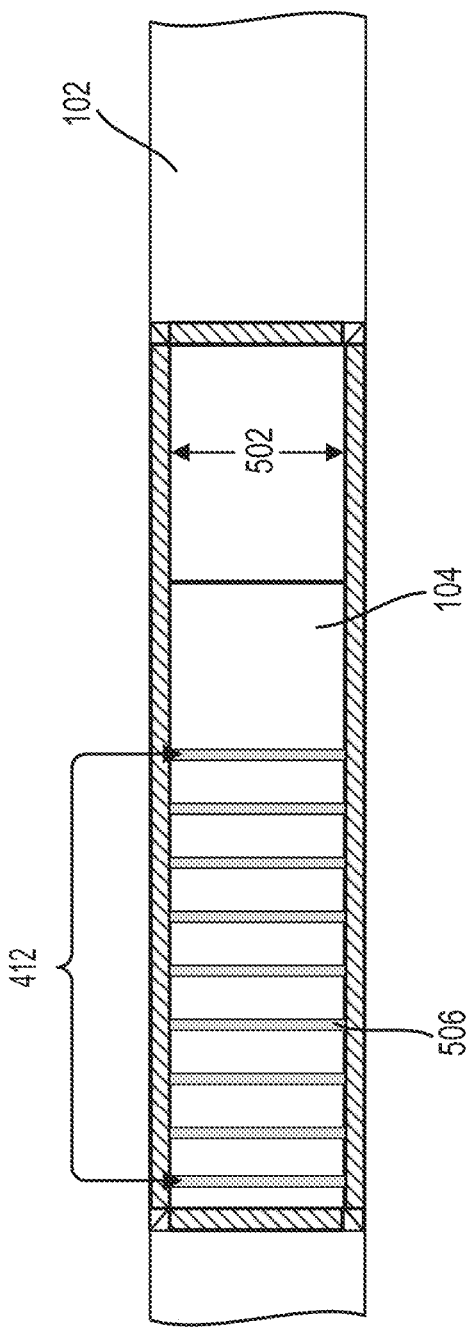
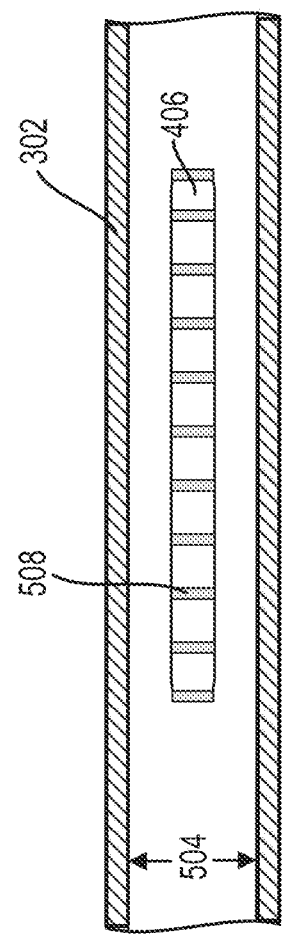
FIG. 5A
FIG. 5B

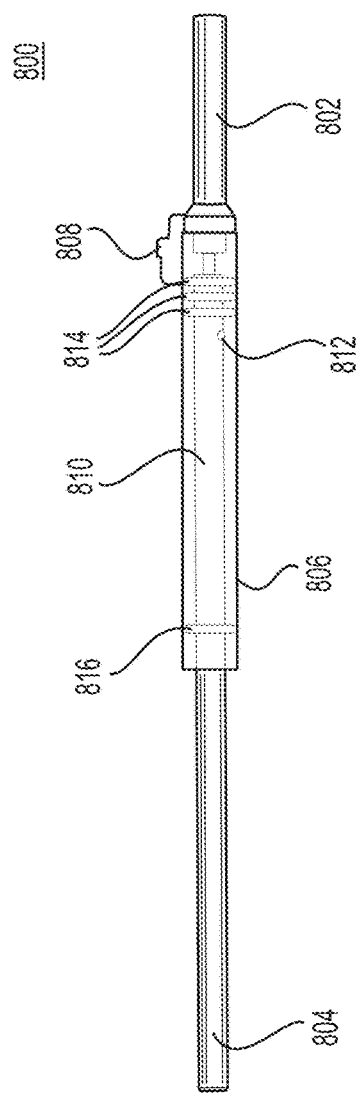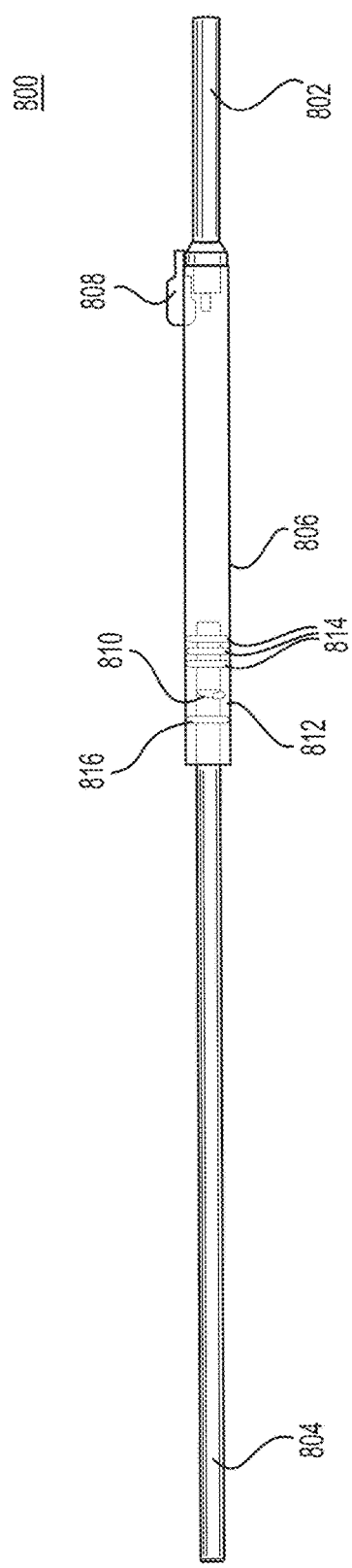

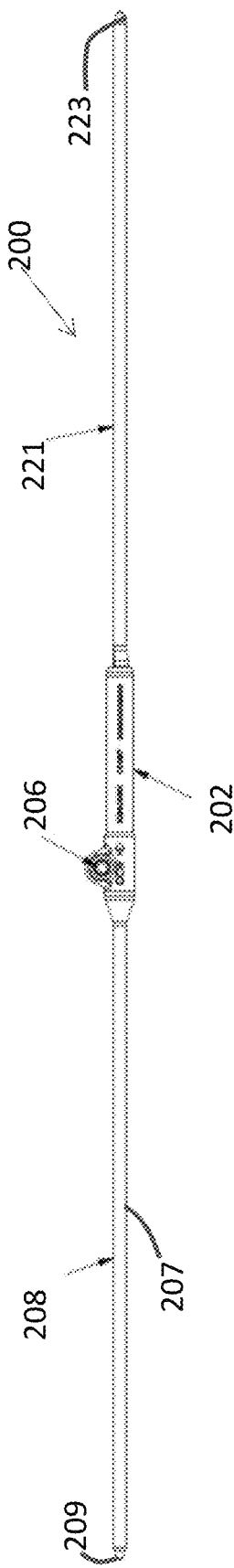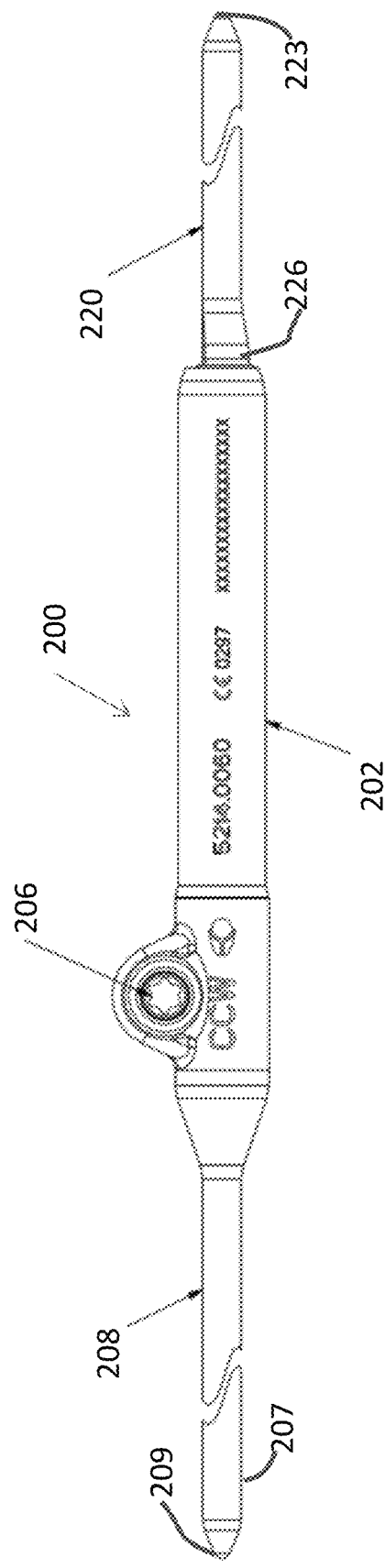
FIG. 24
FIG. 25

GROWING ROD FOR TREATING SPINAL DEFORMITIES AND METHOD FOR USING SAME

REFERENCE TO RELATED APPLICATIONS

The present application is a continuation-in-part of U.S. Ser. No. 15/243,218, filed Aug. 22, 2016, which is a continuation-in-part of U.S. Ser. No. 14/874,771, filed Oct. 5, 2015, both of which are hereby incorporated by reference in their entireties for all purposes.

FIELD OF THE INVENTION

The present invention relates generally to a growing rod for treating spinal deformities, and more particularly to a growing rod that can be secured to a spine of a patient and manually extended to grow with the patient's spine.

BACKGROUND OF THE INVENTION

Scoliosis is a term used to describe any abnormal, sideway curvature of the spine. The most common form of scoliosis for patients between the age of 10 and 18 years is termed adolescent idiopathic scoliosis (AIS). Although the particular cause of this type of scoliosis is still unknown, advancements in the medical field have enabled doctors to increase the likelihood of successfully treating scoliosis is children and adolescents.

Studies have shown that curvatures in the spine progress during the rapid growth period of children. Because of this, children suffering from scoliosis are generally recommended by their doctor to undergo surgical treatment to prevent curve progression and to obtain some curve correction.

One type of spinal surgery for treating scoliosis in children is the use of implantable rods that allow for continued growth of the spine. One or two rods are implanted into the child through the back of the spine. The rods are then secured to the spine above and below the curve using hooks or screws. Because the child will continue to grow after the spinal surgery, the child will be required to return every few months to have the rods lengthened to keep up with his/her growth.

There thus exists a need to provide improved growing rods.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention cures some of the deficiencies in the prior art by providing a growing rod that is less complex and that can be manually extended by a user.

The growing rod of the illustrative embodiment of the present invention is adapted to be subcutaneously implanted and secured along a length of a spine of a patient. The growing rod comprises a base rod, an extendible rod having a distal portion that is slidably coupled to the base rod and arranged with a gear rack, and a distraction unit.

The distraction unit provides one or more mechanical elements to facilitate linear movement of the extendible rod relative to the base rod. In general, the distraction unit comprises: (i) a housing attached to the base rod, (ii) a rotatable drive interface accessible by an external driver from outside of the housing, and (iii) a drive gear mechanism housed within the housing and coupled to the rotatable drive interface and the gear rack such that rotation of the rotatable drive interface causes linear movement of the extendible rod through the gear rack.

Because the patient is likely to continue to grow after implantation of the growing rod, the patient will be required to return to the doctor (e.g., two months, four months, six months, etc., after each doctor's visit) to have the growing rod extended in order to keep up with the patient's growth. This can be accomplished by making a small incision on the patient's back to access the rotatable drive interface with an external driver. The rotatable drive interface is adapted to be physically coupled to and manually rotated by the external driver employed by the doctor. As the doctor rotates the rotatable drive interface in a first direction (e.g., clockwise), it causes linear movement of the extendible rod through the gear rack. The linear movement is a result of a gear in the drive gear mechanism cooperating with the gear rack to linearly move the extendible rod relative to the base rod. A latching mechanism housed within the housing is configured to latch onto the drive gear mechanism to prevent the rotatable drive interface from being able to rotate in a second direction (e.g., counter-clockwise) for retracting the extendible rod. The latching mechanism also provides a means to prevent the drive gear mechanism from causing the extendible rod from retracting under pressure of the spine; for example, when the patient is sitting up, standing, walking, etc.

To unlatch the latching mechanism, provided is a rotatable cam interface arranged on the outside of the housing. The doctor can access the rotatable cam interface by using an external cam driver. Rotating the rotatable cam interface using the driver causes a cam housed within the housing to unlatch the latching mechanism from the drive gear mechanism, thereby allowing the doctor to rotate the rotatable drive interface in the second direction. This feature allows the doctor to fine tune the overall length of the growing rod if the extendible rod has been extended too much.

By providing a manually operated implant that is less complex, like the growing rod of the illustrative embodiment, fewer elements and moving parts can be used to extend and retract the implant without the need of a power source.

In an alternative embodiment of the present invention, different types of gears and gear configurations are employed to extend the extendible rod relative to the base rod.

In a further alternative embodiment of the present invention, the extendible rod is extended relative to the base rod by means of applying fluid pressure through a fluid intake coupled to a fluid connection body of the growing rod. The fluid pressure enters the connection body and forces a piston forwards to extend the extendible rod.

In yet another alternative embodiment, a growing rod is adapted to be extended by incrementally pushing a toggling switch on the surface of a patient's skin.

In still a further alternative embodiment, an implantable growing rod assembly is adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis.

These advantages of the present invention will be apparent from the following disclosure and the appended claims.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

FIG. 1 is a perspective view of a growing rod in a collapsed configuration in accordance with an illustrative embodiment of the present invention.

FIG. 2 is a perspective view of the growing rod of FIG. 1 in a fully extended configuration in accordance with an illustrative embodiment of the present invention.

FIG. 5A depicts an opening arranged on a base rod of the growing rod in accordance with an illustrative embodiment of the present invention.

FIG. 5B depicts an opening arranged on the housing of the distraction unit in accordance with an illustrative embodiment of the present invention.

FIG. 8A is a perspective view of a hydraulic growing rod in a collapsed configuration in accordance with an alternative embodiment of the present invention.

FIG. 8B is a perspective view of the g hydraulic rowing rod of FIG. 8A in a fully extended configuration in accordance with an alternative embodiment of the present invention.

FIG. 24 is a side elevational view of an implantable rod assembly according to an alternative embodiment.

FIG. 25 is an enlarged broken side elevational view of the rod assembly of FIG. 24.

DETAILED DESCRIPTION

Figure 3:
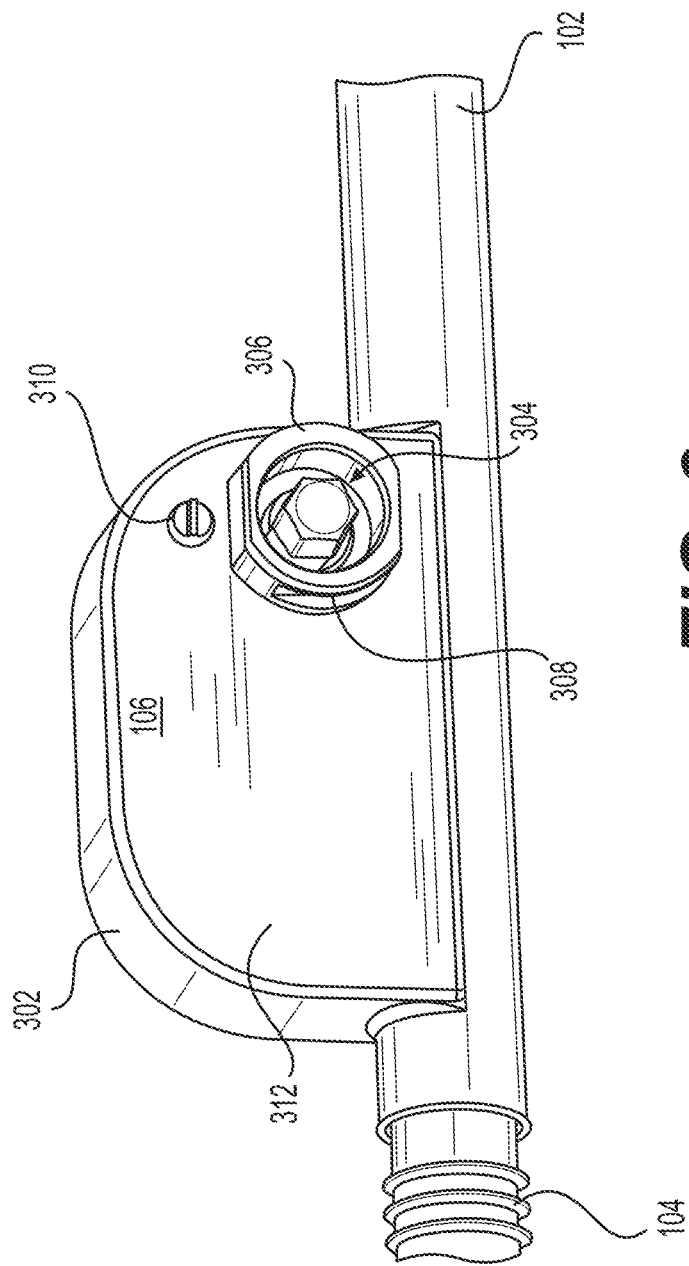
FIG. 3 depicts the outside of a housing of a distraction unit in accordance with an illustrative embodiment of the present invention.

In the drawings, like numerals indicate like elements throughout. Certain terminology is used herein for convenience only and is not to be taken as a limitation on the present device. The terminology includes the words specifically mentioned, derivatives thereof and words of similar import.

The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present device.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required.

FIG. 1 shows a growing rod 100 in a collapsed configuration in accordance with an illustrative embodiment of the present invention. The growing rod comprises: base rod 102, extendible rod 104, and distraction unit 106. Each of these elements that form growing rod 100 can be constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of growing rod 100 is made from a durable thermoplastic polymer, such as polyether ether ketone (PEEK).

In accordance with the illustrative embodiment, extendible rod 104 has a proximal portion that is slidably coupled to base rod 102 and arranged with a gear rack. The extendible rod may be constructed to have a slightly smaller diameter than that of base rod 102 in order to allow the extendible rod to telescopically slide in and out of the base rod. It will be clear to those skilled in the art, after reading this disclosure, how to make and use alternative embodiments of the present invention in which base rod 102 can be adapted to slide in and out of extendible rod 104.

FIG. 2 shows growing rod 100 in a fully extended configuration in accordance with an illustrative embodiment of the present invention. In this figure, extendible rod 104 has been fully extended relative to base rod 102 in response to a doctor manually rotating a rotatable drive interface that is arranged on the outside of distraction unit 106. The doctor can also fine tune the length of growing rod 100 by retracting extendible rod 104 to a desired distraction length. The doctor can achieve this by manually rotating a rotatable cam interface arranged on the outside of distraction unit 106 in the opposite direction. The illustrative embodiment of extendible rod 104 is adapted to allow for a minimum of three and a half years growth before replacement or removal is required. However, it will also be clear to those skilled in the art, after reading this disclosure, how to make and use alternative embodiments in which extendible rod 104 is adapted for more or less than three and a half years growth before replacement or removal is required. These features of the present invention will be described in more detail below, with respect to FIGS. 3 and 4.

FIG. 3 is a perspective view of the outside of distraction unit 106 in accordance with an illustrative embodiment of the present invention. The distraction unit comprises: housing 302, rotatable drive interface 304, guide wall 306, recess 308, rotatable cam interface 310, and cover plate 312. Each of these elements of distraction unit 106 can be constructed from a biocompatible plastic, metal, metal alloy, or combination thereof. The biocompatible metals and metal alloys can be, for example, and without limitation, titanium, titanium alloy, stainless steel, cobalt chrome, or any combination thereof.

As shown in the figure, rotatable drive interface 304 is arranged on the outside of housing 302 and is accessible to a doctor via an external driver. The rotatable drive interface 304 is hexagon-shaped and is adapted to be received in a correspondingly shaped recess of the external driver. The rotatable drive interface 304 can be, for example, and without limitation a 35 mm hex drive interface. Although rotatable drive interface 304 is depicted as hexagon-shaped, it will be clear to those skilled in the art, after reading this disclosure, how to make and use alternative embodiments of the present invention in which rotatable drive interface 304 can have any shape and size, so long as it can be received by the recess of the external driver.

As further shown in the figure, rotatable drive interface 304 is surrounded by guide wall 306, which has a pair of oppositely positioned recesses 308 arranged on the outer surface of the guided wall. Only one recess 308 is shown in the figure, but it will be clear to those skilled in the art, after reading this disclosure, that one half of guide wall 306 is substantially a mirror image of the other half of the guide wall. In accordance with the illustrative embodiment, each recesses 308 is adapted to receive a correspondingly shaped and sized protrusion, hook, etc., arranged on the external driver. Once received, the external driver is locked to guide wall 306 such that lateral movement of the external driver is prevented. This mechanism helps prevent the external driver from dislodging from rotatable drive interface 304 as the doctor is rotating it. The physical structure of guided wall 306 also has the added benefit of helping the doctor determine where rotatable drive interface 304 might be located underneath the skin.

Housing 302 also includes rotatable cam interface 310, which is coupled to a cam housed within housing 302. Although the figure depicts rotatable cam interface 310 as having a slotted head for receiving a corresponding shaped external cam driver, it will be clear to those skilled in the art, after reading this disclosure, that rotatable cam interface 310 can have any shape and size, so long as it can receive the external cam driver. As will be discussed in more detail below, with reference to FIG. 4, rotating interface 310 causes a cam housed within housing 302 to disengage a latch from a drive gear mechanism so that a doctor can retract extendible rod 104.

Figure 4:
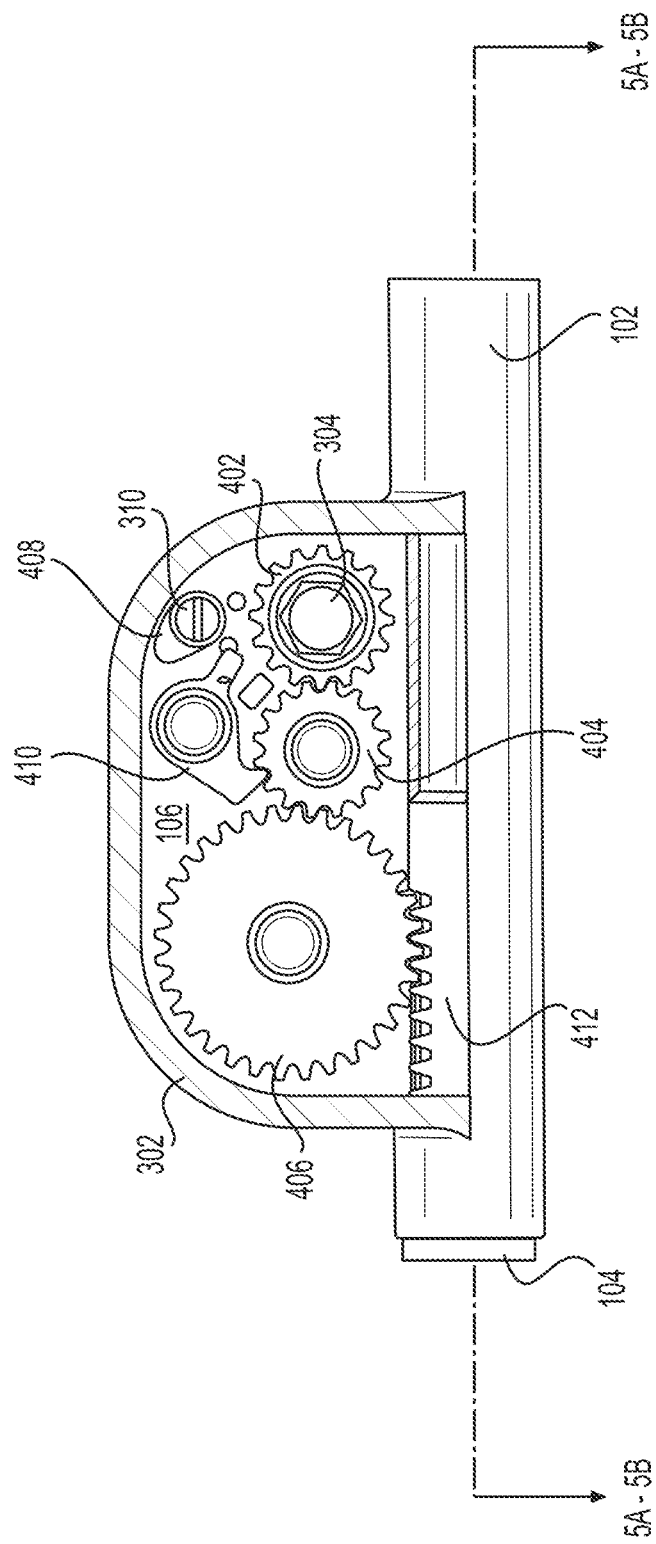
FIG. 4 depicts the inside of the housing of the distraction unit in accordance with an illustrative embodiment of the present invention.

FIG. 4 is a cross-sectional view of the interior of distraction unit 106, thus housing 302, in accordance with an illustrative embodiment of the present invention. The interior of the distraction unit comprises: drive gear 402, idler gear 404, pinion 406, cam 408, and latch 410. Like all of the elements that form growing rod 100, elements 402 to 410 can be constructed from a biocompatible plastic, metal, metal alloy, or combination thereof. The biocompatible metals and metal alloys can be, for example, and without limitation, titanium, titanium alloy, stainless steel, cobalt chrome, or any combination thereof.

Removing cover plate 312 from housing 302 reveals a drive gear mechanism that is coupled to rotatable drive interface 304 and gear rack 412. The gear rack 412 is preferably arranged on a proximal portion of extendible rod 104, but it will be clear to those skilled in the art, after reading this disclosure, how to make and use alternative embodiments of the present invention in which gear rack 412 is arranged along the length of extendible rod 104.

In accordance with the illustrative embodiment, the drive gear mechanism comprises drive gear 402, idler gear 404, and pinion 406. These gears are coupled to one another as shown in the figure to form a "simple gear train". The gear ration between drive gear 402 and pinion 406 is preferably 2-to-1 (i.e., 2:1 ratio). What this means is that pinion 404 has twice as many teeth as drive gear 402. However, those skilled in the art will appreciate after reading this disclosure that distraction unit 106 can be configured to have any number of gears and different gear ratio ranges without departing from the scope of the invention. For example, the gear ratio range can have a lower limit of 1.5 and an upper limit of 10.

Furthermore, although FIG. 4 only depicts the drive gear mechanism as having three gears, it will be clear to those skilled in the art, after reading this disclosure, how to make and use alternative embodiments of the present invention in which the drive gear mechanism has fewer or more gears than depicted. For example, and without limitation, the drive gear mechanism can have one gear, two gears, ten gears, etc., without departing from the scope of the present invention. It will also be clear to those skilled in the art that other types of gears and gear trains could be used without departing from the scope of the present invention. Other types of gears may include, for example, and without limitation, spur gears, helical gears, herringbone gear, face gears, screw gears, etc., or a combination thereof. Other types of gear trains may include, for example, and without limitation, compound gear trains, reverted gear trains, epicyclic gear train, etc., or a combination thereof. Lastly, it will be clear to those skilled in the art, after reading this disclosure, how to make and use alternative embodiments of the present invention in which distraction unit 106 can be configured to have different number of gears and different gear ratios without departing from the scope of the invention.

As briefly described above, rotatable drive interface 304 is adapted to be accessed by an external driver from outside of housing 302. The rotatable drive interface is also adapted to be physically coupled to and manually rotated by the external driver for extending and retracting the extendible rod relative to the base rod. More specifically, rotating interface 304 in a first direction (e.g., clockwise) rotates drive gear 402 in the same direction. In response to the rotational movement of drive gear 402, idler gear 404 will also begin to rotate, but in the opposite direction, while pinion 406 will rotate in the same direction as drive gear 402. Thus, gears 402, 404, and 406 are coupled to rotatable drive interface 304 in such a way that rotation of the rotatable drive interface causes each of the gears to simultaneously rotate. The rotational movement from gears 402, 404, and 406 is then translated into linear movement by coupling pinion 406 to gear rack 412.

The coupling between pinion 406 and gear rack 412 is made possible by coupling housing 302 of distraction unit 106 to base rod 102 as shown in FIGS. 2 and 3. More specifically, and as shown in FIG. 5A, the outer surface of base rod 102 is machined with an opening 502. The opening 502 is arranged at a distal portion of base rod 102. The opening 502 can also be seen in FIG. 4. Similarly, housing 302 has an opening 504 arranged on one side of the housing. The opening 504 of housing 302 is shown in FIG. 5B. In accordance with the illustrative embodiment, the teeth 508 of pinion 406 extend slightly outside of opening 504 of housing 302. This allows the teeth 508 of pinion 406 to extend through opening 502 of base rod 102 to engage the teeth 506 of gear rack 412 when housing 302 is coupled to base rod 102, thereby forming a rack-and-pinion configuration. As discussed above, rotational movement of pinion 406 is translated into linear movement by gear rack 412 such that extendible rod 104 can be either extended or retracted, depending on which direction rotatable drive interface 304 is rotated.

Referring back to FIG. 4, the latching mechanism housed within housing 302 is adapted to latch onto a gear of the drive gear mechanism such that rotation of rotatable drive interface 304 is prohibited in a direction (e.g., in a counter-clockwise direction) that retracts extendible rod 104. In accordance with the illustrative embodiment, the latching mechanism comprises latch 410, which is biased to lock the drive gear mechanism. As shown in the figure, latch 410 is biased to latch onto and lock idler gear 404. Although latch 410 is biased to lock idler gear 404 in the illustrative embodiment, it will be clear to those skilled in the art, after reading this disclosure, how to make and use alternative embodiments of the present invention in which latch 410 is biased to lock drive gear 402 or pinion 406 instead.

Continuing with the illustrative embodiment, latch 410 is sized and shaped to be received between a pair of adjacent teeth of idler gear 404. Latch 410 is spring-loaded in the illustrative embodiment and is adapted to ratchet back and forth as rotatable drive interface 304 is rotated in the clockwise direction for extending rod 104. However, the size and shape of latch 410 relative to the root/pitch of idler gear 404 prevents latch 410 from being able to ratchet back and forth when rotatable drive interface 304 is rotated in the counter-clockwise direction for retracting rod 104. That is, latch 410 will not be dislodged from between the pair of adjacent teeth of idler gear 404 when rotatable drive interface 304 is rotated in a direction that retracts extendible rod 104. This feature of the present invention is advantageous in that downward pressure exerted on the spine (e.g., when the patient is sitting up, standing, etc.) after implantation of growing rod 100 will not cause gears 402, 404, 406 to unintendedly rotate and inadvertently retract rod 104.

Figure 6:
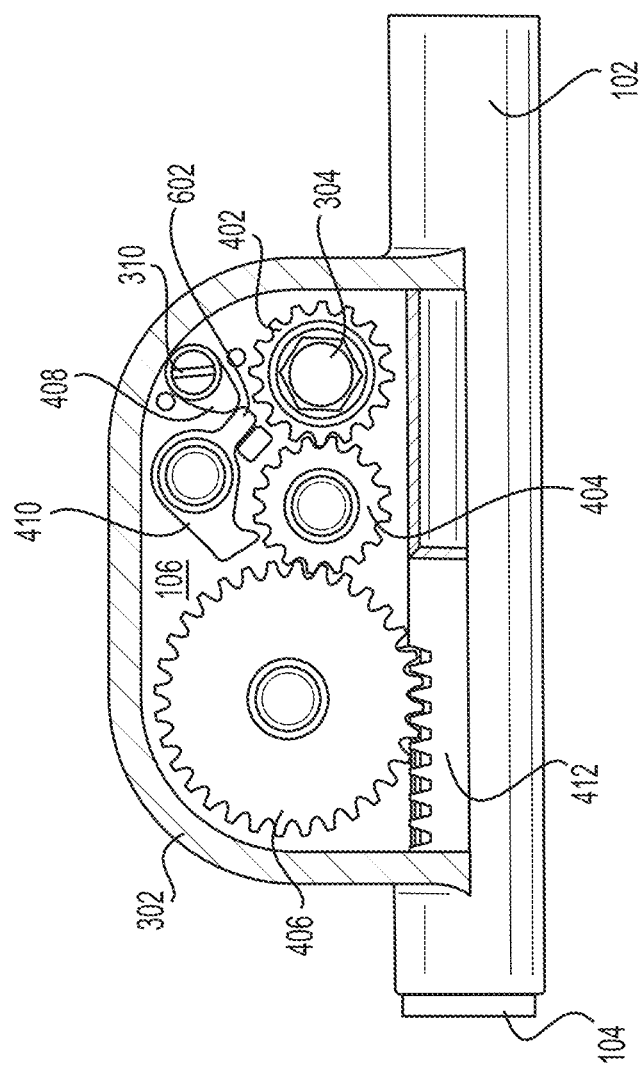
FIG. 6 depicts a cam and a latch configuration for allowing an extendible rod of the growing rod to be retracted.

FIG. 6 shows latch 410 unlatched from between the pair of adjacent teeth of idler gear 404 in accordance with the illustrative embodiment. To unlatch latch 410, rotatable cam interface 310 is provided. The rotatable cam interface is accessible by an external cam driver from outside of housing 302. The rotatable cam interface 310 is coupled to cam 408 such that rotation of the rotatable cam interface causes the latching mechanism to either prohibit or allow the drive gear mechanism to rotate in a direction that retracts or extends the extendible rod 104.

Specifically, rotatable cam interface 310 is adapted to be physically coupled to and manually rotated by external cam driver 310 such that rotation of rotatable cam interface 310 causes a tip of cam 408 to engage or be free from physical contact with latch 410. The rotatable cam interface 310 is rotatable from outside of housing 302 in a first direction (e.g., counter-clockwise) until the tip of cam 310 abuts against lever 602 of latch 410 and pins it against stopper 604. This causes latch 410 to be unlatched from between the pair of adjacent teeth of idler gear 404. This also holds latch 410 in the unlatched position so that the doctor can rotate interface 304 to retract extendible rod 104 to a desired length. After reaching the desired length, the doctor can use the external cam driver to rotate interface 310 in a second direction (e.g., clockwise) to position latch 410 between a pair of adjacent teeth of idler gear 404, thereby locking gears 402, 404, and 406 from rotating in a direction that retracts extendible rod 104.

Having described the elements of growing rod 100 in particular detail, an example of using growing rod 100 will now be described. After growing rod 100 has been implanted into a patient, the patient may be required to return to the doctor every few months to have growing rod 100 extended to keep up with his/her growth. To extend growing rod 100, the doctor uses his hands to feel for where distraction unit 106 is located; in particular, where guide wall 306 is located underneath the patient's skin. Once located, a small incision is made on the patient's back near guide wall 306. An external driver is inserted through the small incision and then physically coupled to rotatable drive interface 304 from outside of housing 302. Once coupled, the doctor may manually rotate rotatable drive interface 304 using the coupled external driver. As discussed above, with respect to FIGS. 3-6, rotating interface 304 also rotates drive gear 402, idler gear 404, and pinion 406, since each of these gears are either physically or indirectly coupled to rotatable drive interface 304. The rotational movement of these gears is then translated into linear movement through the rack-and-pinion configuration created by coupling pinion 406 to gear rack 412. The linear movement of gear rack 412 causes extendible rod 104 to linearly extend relative to base rod 102. Likewise, rotating interface 304 in the opposite direction causes extendible rod 104 to linearly retract relative to base rod 102, as discussed above, with respect to FIGS. 3-6.

It should be noted that "manual" rotation of rotatable drive interface 304 includes, for example, and without limitation, physically coupling the external driver to rotatable drive interface 304 and then having the doctor manually rotate the physically coupled external driver in a clockwise or counter-clockwise direction. In this embodiment, the external driver is similar to, for example, and without limitation, a socket wrench that is not electrically driven.

In alternative embodiments, "manual" rotation of rotatable drive interface 304 includes, for example, and without limitation, physically coupling the external driver to rotatable drive interface 304 and then actuating one or more buttons to electrically power the physically coupled external driver. In this embodiment, a power source provides electricity of the physically coupled external driver to manually rotate interface 304.

Figure 7A:
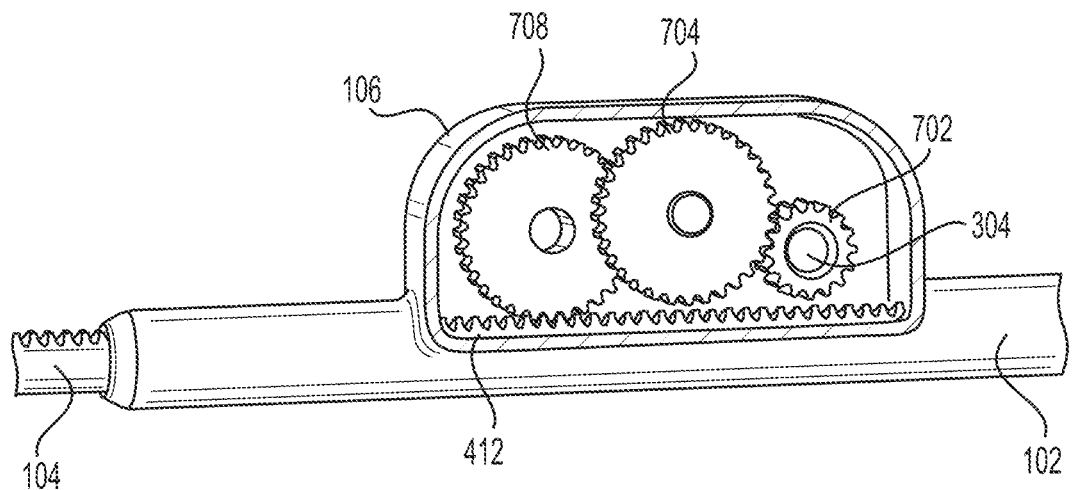
FIG. 7A depicts an extendible rod having a gear train that shows one side of a compound gear in accordance with an alternative embodiment of the present invention.
Figure 7B:
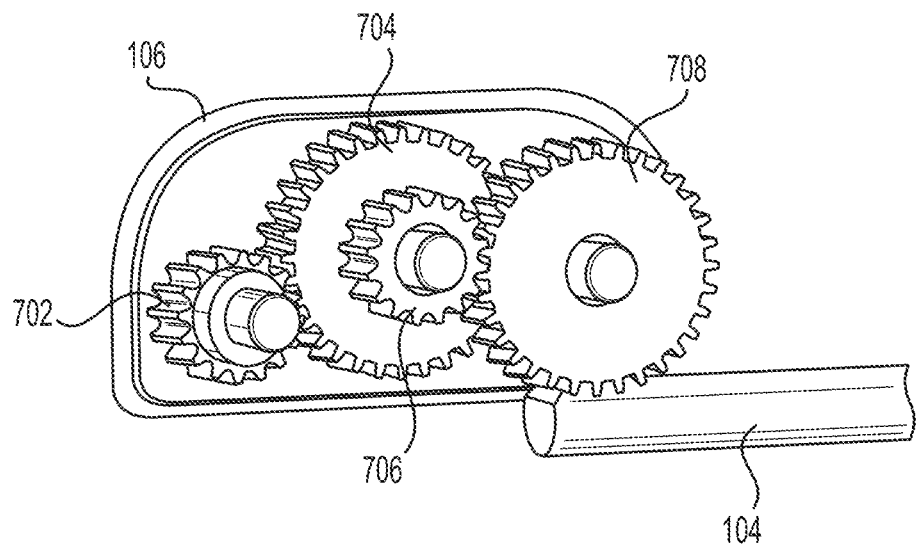
FIG. 7B depicts the other side of the gear train of FIG. 7A in accordance with an alternative embodiment of the present invention.

FIGS. 7A and 7B depict an alternative embodiment of extendible rod 104 discussed above. FIG. 7A depicts one side of housing 302 of distraction unit 106 with cover plate 312 removed. Housed within housing 302 in this alternative embodiment are four gears—namely, drive gear 702, a compound gear formed by a larger gear 704 having a smaller gear 706 coupled on one side of the larger gear, and pinion 708. The smaller gear 706 is shown in FIG. 7B.

In accordance with this alternative embodiment, drive gear 702 is coupled to larger gear 704 (as shown in FIG. 7A) and smaller gear 706 is coupled to pinion 708 (as shown in FIG. 7B). Pinion 708 in turn is coupled to gear rack 412, as discussed above, with respect to FIGS. 3-5B. The gear configuration in this alternative embodiment has, for example, and without limitation, a gear ratio of 4-to-1 (i.e., 4:1 ratio). However, those skilled in the art will appreciate after reading this disclosure that distraction unit 106 can be configured to have different number of gears and different gear ratios without departing from the scope of the invention.

To extend or retract extendible rod 104 relative to base rod 102, rotatable drive interface 304 can be respectively rotated in a clockwise or a counter-clockwise direction, as discussed above, with respect to FIGS. 3-5B. As interface 304 rotates drive gear 702, the larger gear 704 and smaller gear 706 also rotate, but in the opposite direction of drive gear 702. The coupling between smaller gear 706 and pinion 708 causes linear movement of extendible rod 104 through gear rack 412, as discussed above. Although FIGS. 7A and 7B do not depict the latching mechanism (e.g., latch 410, rotatable cam interface 310, cam 408, stopper 604, etc.) discussed above, those skilled in the art will appreciate that this alternative embodiment can be configured to include the latching mechanism. The advantage of having a gear train that includes a compound gear is the ability to more easily meet the distraction force for extending extendible rod 104.

FIG. 8A shows a growing rod 800 in a collapsed configuration in accordance with an alternative embodiment of the present invention. The growing rod comprises: base rod 802, extendible rod 804, fluid connector body 806, fluid intake 808, piston 810, spring-loaded ball 812, fluid seals 814, end seal 816, input tube 818, and port 820.

FIG. 8B shows growing rod 800 in a fully extended configuration in accordance with an alternative embodiment of the present invention. As will be discussed in more detail below, with respect to FIG. 9, extendible rod 804 has been fully extended relative to base rod 802 in response to fluid pressure being applied through fluid intake 808 to force piston 812 forwards.

Figure 9:
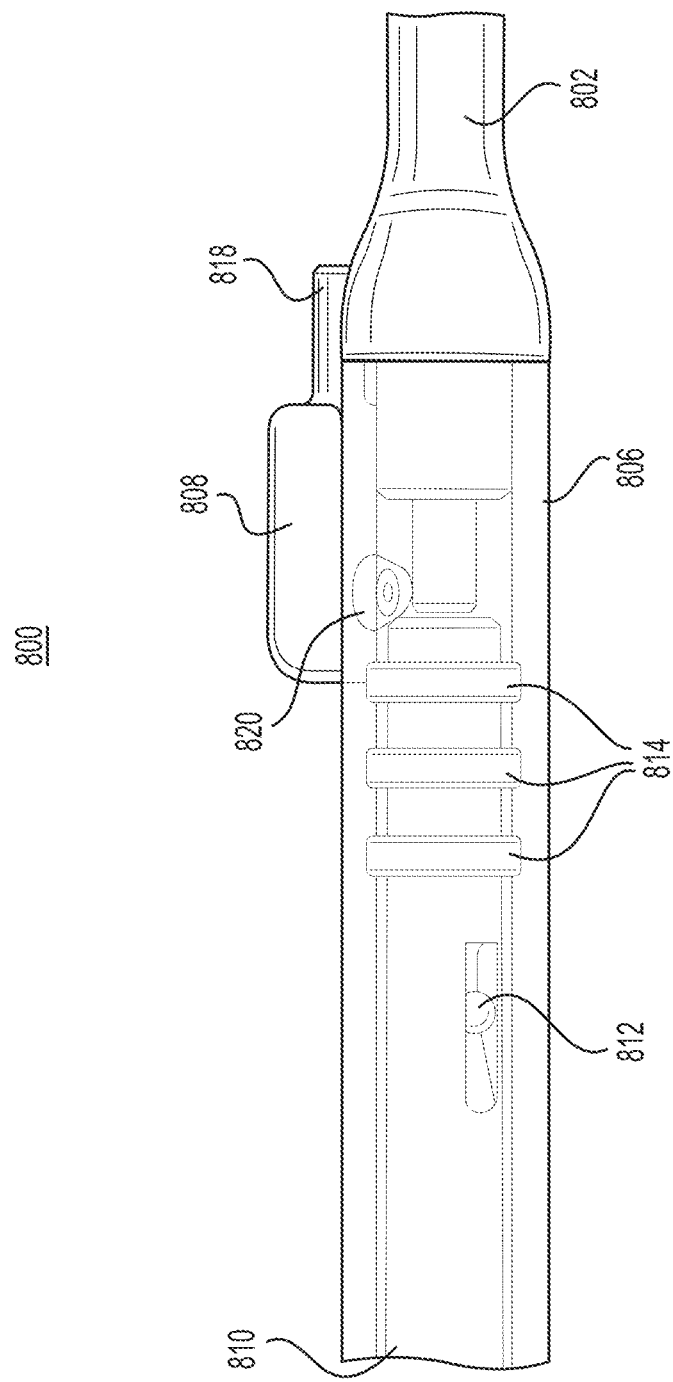
FIG. 9 is an exploded view of the fluid connection body, fluid intake, and piston for extending an extendible rod through fluid pressure in accordance with an alternative embodiment of the present invention.

Turning now to FIG. 9, and in accordance with this alternative embodiment, growing rod 800 is implanted along a spine of a patient and can be expanded after implantation to keep up with the growth of the patient. More specifically, growing rod 800 can be expanded by making a small incision on the patient's back to access an input tube 818 arranged on fluid intake 808, which fluid intake is coupled to connector body 806 of growing rod 800. Once accessible, a fluid hose coupled to a fluid delivery device is connected to input tube 818 of fluid intake 808. The fluid delivery device is then operated to apply fluid pressure (e.g., saline fluid, etc.) through fluid intake 808. The fluid pressure exits port 820 and forces piston 812 forwards, thereby extending rod 804 relative to base rod 802. Although three fluid seals are shown in the figures, it will be clear to those skilled in the art, after reading this disclosure, how to make and use alternative embodiments of the present invention in which piston 810 has more or less fluid seals than depicted. It should also be noted that growing rod 800 has an end seal 816 that prevents extendible rod 804 from being able to extend too far and decoupling from connector body 806.

Once extendible rod 804 has reached a desired distraction length, extendible rod 804 will be under load pressure. This load pressure will force extendible rod 804 to retract backwards on itself. At this time, spring-loaded ball 812 is forced up a ramp arranged within a recess of on piston 810. This causes ball 812 to press up against the side of fluid connector body 806, thereby stopping any further retraction of extendible rod 804. Once extendible rod 804 has been stopped from retracting on itself, the fluid pressure can be relieved from an access port to empty fluid connector body 806 of the fluid pressure.

The design of growing rod 800 is advantageous because it has a small diameter and is of minimal design complication. Growing rod 800 is also advantageous because the fluid pressure will not be in effect during implantation—that is, fluids and pressure will only be introduced when extendible rod 804 is being extended relative to base rod 802. From this design, growing rod 800 is able to be a passive growth mechanism. As the spine grows, growing rod 800 can be advanced within the patient without the aid of external manipulation. The fact that growing rod 800 can be both passive and manipulative (if required) reduces the need of additional surgeries for the patient.

Figure 10:
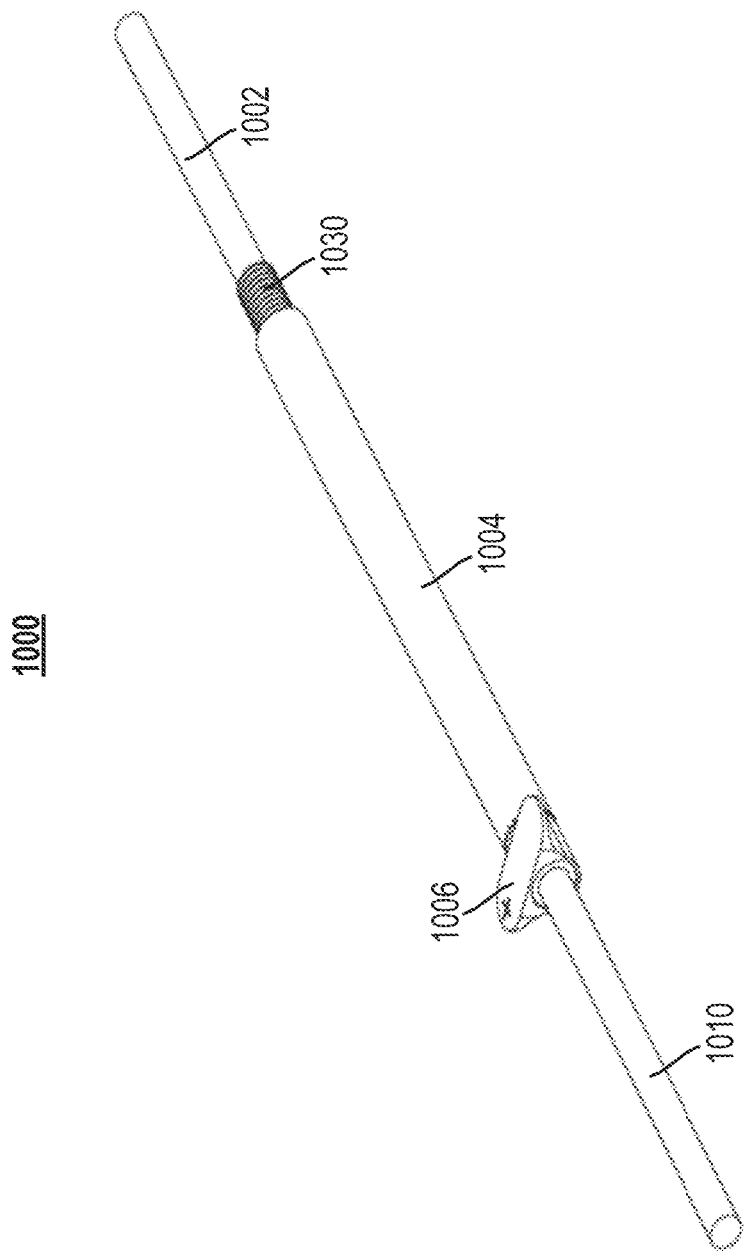
FIG. 10 is a perspective view of a growing rod in accordance with yet another alternative embodiment of the present invention.

FIG. 10 depicts a further alternative embodiment of the present invention. Growing rod 1000 comprises: extendible rod 1002, coupling 1004, toggling switch 1006, spring 1008, and base rod 1010. Each of these elements that form growing rod 1000 can be constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of growing rod 1000 can be made from a durable thermoplastic polymer, such as polyether ether ketone (PEEK).

In accordance with this alternative embodiment, the outer surface of extendible rod 1002 is arranged with threads 1030. Preferably, only a portion of the outer surface of extendible rod 1002 is threaded with threads 1030. However, in other embodiments, the entire length of extendible rod is arranged with threads 1030. The proximal portion of extendible rod 1002 is adapted to be received within and threaded into the distal portion of coupling 1004.

Figure 12:
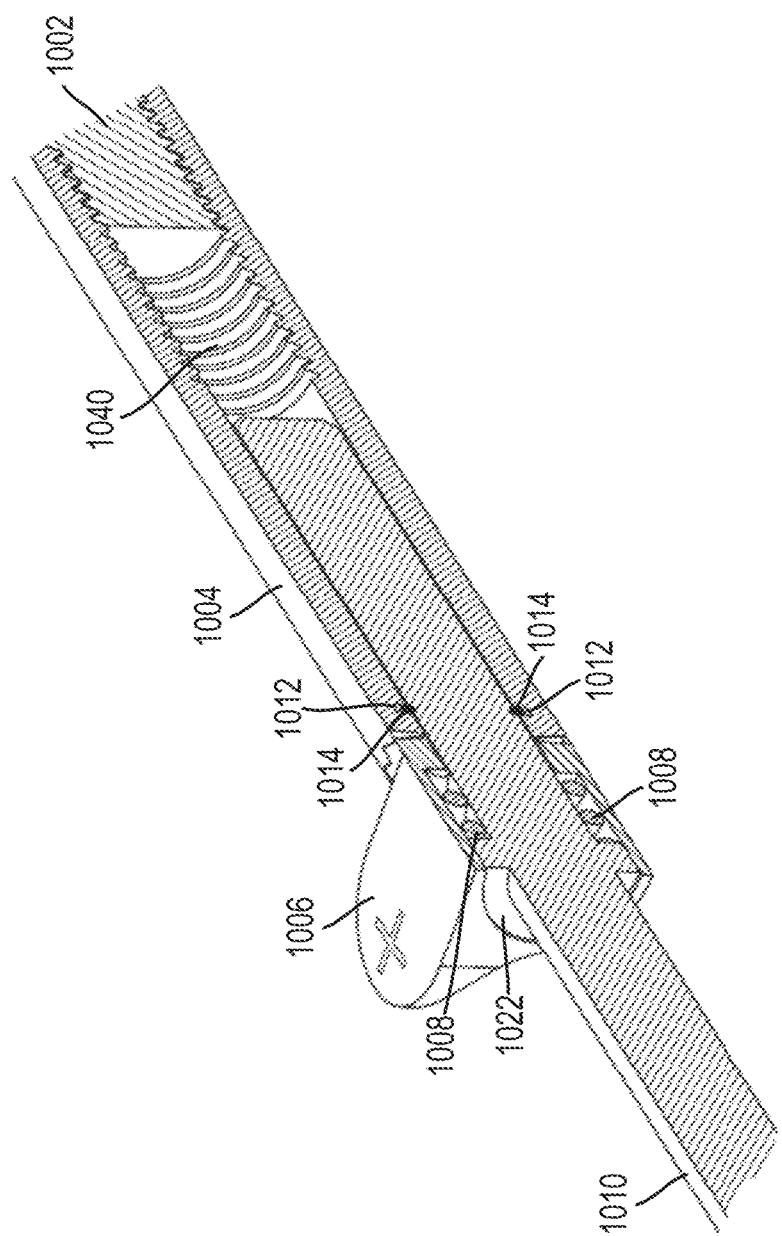
FIG. 12 is a cross-sectional view of the growing rod of FIG. 10.

Coupling 1004 has a through-hole for receiving extendible rod 1002 and base rod 1010. As shown in FIG. 12, the inner surface of the distal portion of coupling 1004 is arranged with threads 1040. These threads of coupling 1004 allow extendible rod 1002 to be received within and threaded into the distal portion of coupling 1004. The inner surface of the proximal portion or intermediate portion of coupling 1004 is arranged with a groove 1012. The groove is adapted to receive a retaining ring 1014 coupled to base rod 1010 for preventing the base rod from being able to slide in and out of the through-hole of coupling 1004.

Figure 11:
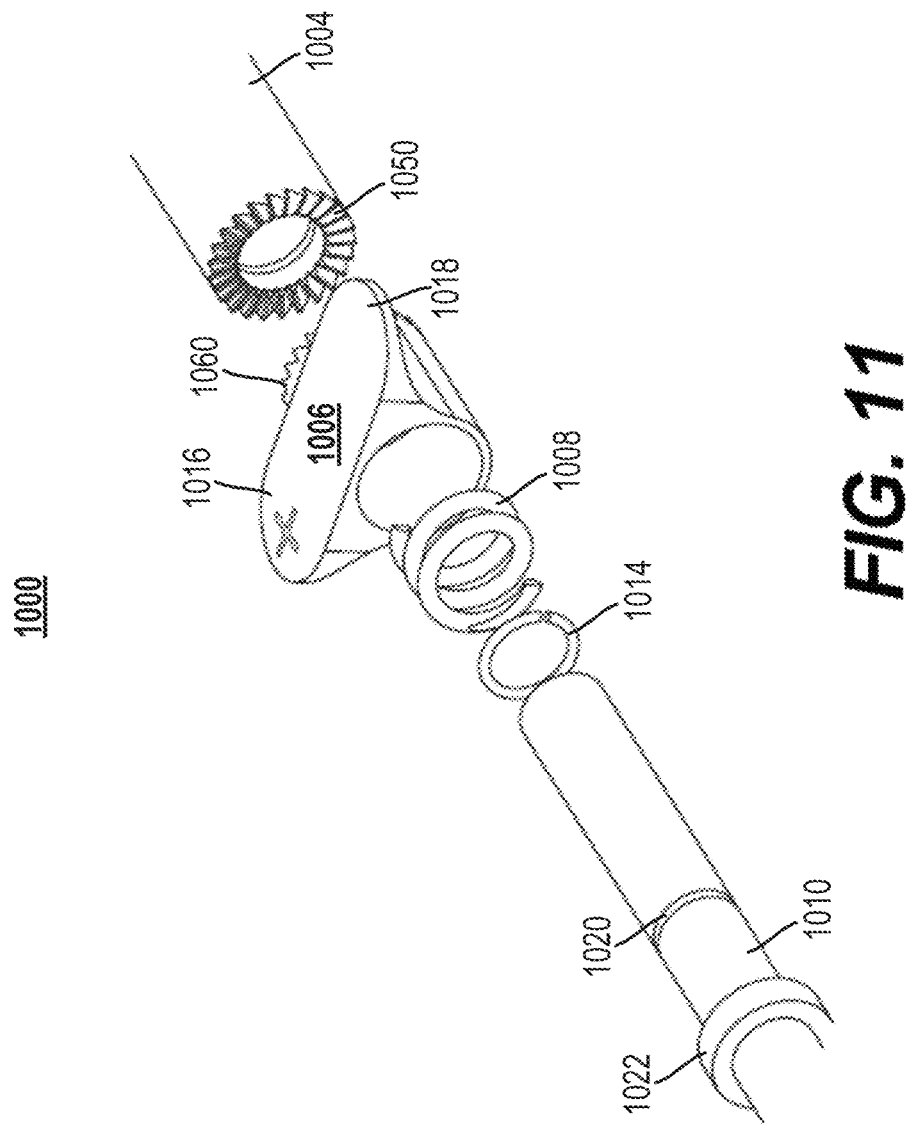
FIG. 11 depicts the elements that form the growing rod of FIG. 10.
Figure 13:
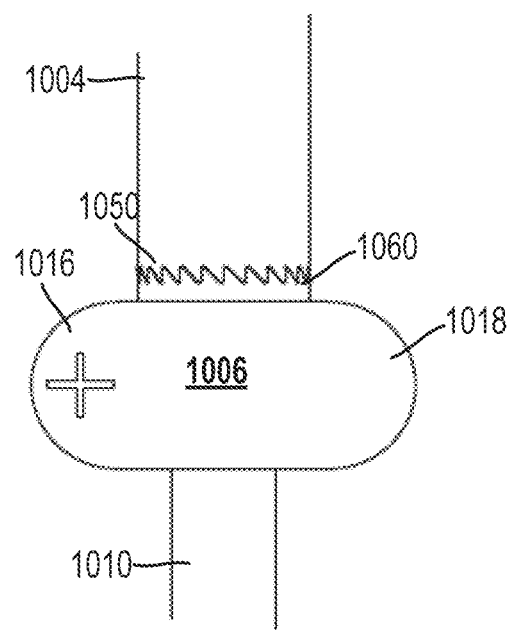
FIG. 13 depicts the one-way, sliding, sawtooth clutch for extending the growing rod of FIG. 10.

As further shown in FIGS. 11 and 13, the proximal portion of coupling 1004 is arranged with teeth 1050 that are adapted to mesh with the teeth 1060 of toggling switch 1006 to form a one-way, sliding, sawtooth clutch. The teeth of coupling 1004 and toggling switch 1006 are chamfers having a symmetrical sloping edge, as shown in the figures. The sloping edge allows teeth 1050 of coupling 1004 to slide along the sloping edge of the teeth 1060 arranged on toggling switch 1006. The angle of the sloping edge of the teeth of elements 1004 and 1006 can be, for example, and without limitation, 10°, 45°, 65°, etc. As will be discussed in more detail below, the one-way, sliding, sawtooth clutch allows coupling 1004 to rotate and cause linear movement of extendible rod 1002.

Toggling switch 1006 is arranged with a through-hole for receiving base rod 1010. The inner surface of the through-hole of toggling switch 1006 has a cutout that is adapted to receive spring 1008. Toggling switch 1006 is also arranged with a first toggle 1016 and a second toggle 1018 that can be operated by a user (e.g., a doctor, nurse, etc.) to cause linear movement of extendible rod 1002 relative to coupling 1004.

The distal portion of base rod 1010 is arranged with a groove 1020 for receiving retaining ring 1014. As discussed above, retaining ring 1014 is adapted to prevent base rod 1010 from being able to slide in and out of the through-hole of coupling 1004 when seated within groove 1012. The proximal portion of base rod 1010 is arranged with a circular protrusion having an underside that is adapted to abut against spring 1008.

The method of using growing rod 1000 will now be described. After growing rod 1000 has been implanted along the spine of a patient, the growing rod will need to be periodically extended to keep up with the patient's growth. Unlike the other embodiments described in this disclosure, this alternative embodiment does not require making any incisions on the patient's back access a mechanism for extending the length of growing rod 1000. Instead, the doctor can simply use his hands and feel where toggling switch 1006 is located underneath the patient's skin on his/her back. Once the doctor has located toggling switch 1006, the first toggle 1016 or the second toggle 1018 can be operated by the doctor to lengthen growing rod 1000. For the purpose of this discussion, and without limitation, the first toggle 1016 will be used to lengthen growing rod 1000.

More specifically, the doctor can press on the first toggle 1016 one or more times on the surface of the patient's skin. This pressing action causes toggling switch 1006 to incrementally rotate in the same direction in which the first toggle 1016 is pressed; for example, in a clockwise direction. As toggling switch 1006 incrementally rotates in a clockwise direction, the teeth 1060 of toggling switch 1006 will abut against the teeth 1050 of coupling 1004, thereby driving the coupling to rotate as well. Because coupling 1004 is threaded to base rod 1002, rotating coupling 1004 in this way causes extendible rod 1002 to back out of the through-hole of the coupling, thus extending the length of growing rod 1000.

However, it should be noted that pressing on the second toggle 1018 will not cause coupling 1004 to rotate in the opposite direction; in other words, a counter-clockwise direction. This is because the teeth 1050 of coupling 1004 and the teeth 1060 of toggling switch 1006 cooperatively form a one-way, sliding, sawtooth clutch. More specifically, as the second toggle 1018 is pressed by the doctor, the sloping edge of the teeth 1060 of toggling switch 1006 slide along the sloping edge of the teeth 1050 of coupling 1004. This causes toggling switch 1006 to be pushed away from coupling 1004 and compress against spring 1008. Spring 1008 is then compressed against the underside of circular protrusion 1022 until the teeth 1060 of toggling switch 1006 is once again meshed with the teeth 1050 of coupling 1004.

As noted above, this alternative embodiment is advantageous in that no incisions are required to extend the growing rod.

Figure 14:
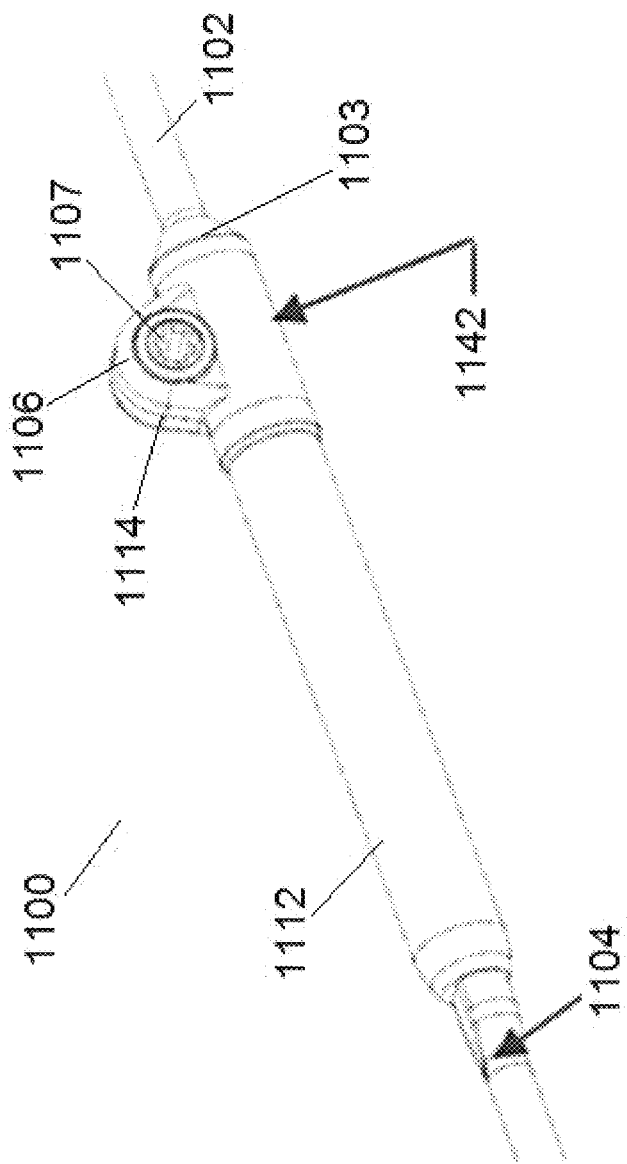
FIG. 14 is a top perspective view of an alternative growing rod in accordance with some embodiments.

FIG. 14 is a top perspective view of an alternative growing rod in accordance with some embodiments. The growing rod 1100 is a manually driven growing rod that advantageously uses a worm gear to extend the length of the growing rod. The advantageous of using such a worm gear is that it prevents inadvertent rotation of any particular gears, thereby reducing the risk of undesired movement of the growing rod.

The growing rod 1100 comprises a fixed rod 1102 and an expansion or extendible rod 1104, wherein the extendible rod 1104 is capable of extending in length away from the fixed rod 1102. The growing rod 1100 further comprises a housing 1112 operably connected to a cover plate 1142 for receiving the fixed rod 1102 and/or extendible rod 1104 therein. The cover plate 1142 is further designed to house one or more gears as part of a gear set 1106 for causing extension and/or retraction of the extendible rod 1104.

As shown in FIG. 14, the growing rod 1100 comprises a fixed rod 1102 and an extendible rod 1104. In some embodiments, the fixed rod 1102 comprises a shaft that is configured to have a fixed length relative to the housing 1112 and/or cover plate 1142. The fixed rod 1102 comprises an end cap 1103 that is operably attached to the cover plate 1142. In contrast, the extendible rod 1104 is configured to have an adjustable length relative to the housing 1112 and/or cover plate 1142. The extendible rod 1104 is capable of expansion via rotation of a rotatable drive interface 1107 in a first direction, and retraction via rotation of the rotatable drive interface 1107 in a second direction opposite the first direction. In some embodiments, the extendible rod 1104 comprises an outer threaded portion (shown as reference numeral 1321 in FIG. 21) that is configured to engage an inner threaded portion of an inner threaded sleeve 1132. This engagement between the threaded portions accommodates lateral movement of the extendible rod 1104 upon rotation of the inner threaded sleeve 1132.

The extendible rod 1104 is received in the hollow shaft of an inner threaded sleeve 1132 (shown in FIG. 15), which itself is received in the hollow shaft of housing 1112. The housing 1112 comprises a hollow body which advantageously encloses a portion of the extendible rod 1104, thereby protecting it from interference with tissue and other objects in the body. On a first end of the housing 1112, an extendible rod 1104 extends there through. On a second end of the housing 1112, a cover plate 1142 is operably attached to the housing 1112. The cover plate 1142 is designed to house and protect a gear set 1106.

In the present embodiment, the gear set 1106 comprises a worm gear set. The worm gear set 1106 comprises a worm in the form of a rotatable drive interface 1107 that is engaged to worm gear 1108 (shown in FIG. 15). Advantageously, a worm gear helps to hold the position of the growing rod 1100 so that it does not inadvertently retract. Rotation of the rotatable drive interface 1107 in a first direction causes rotation of the worm gear 1108 to rotate around a longitudinal axis of the growing rod 1100. The rotatable drive interface 1107 is visible through an eyelid 1114 that is formed in the cover plate 1142 of the growing rod 1100. In some embodiments, the worm gear 1108 is attached to the inner threaded sleeve 1132. In some embodiments, the worm gear 1108 is welded to the inner threaded sleeve 1132. Accordingly, rotation of the rotatable drive interface 1107 in a first direction causes the worm gear 1108 to rotate, which in turn causes rotation of the inner threaded sleeve 1132. As the inner threaded sleeve 1132 is engaged with the extendible rod 1104 via threading, this causes the extendible rod 1104 to translate linearly (e.g., extend or expand). Rotation of the rotatable drive interface 1107 in a second direction causes the worm gear 1108 to rotate in the opposite direction, which in turn causes linear translation of the extendible rod 1104 in an opposite, retracted direction.

Figure 15:
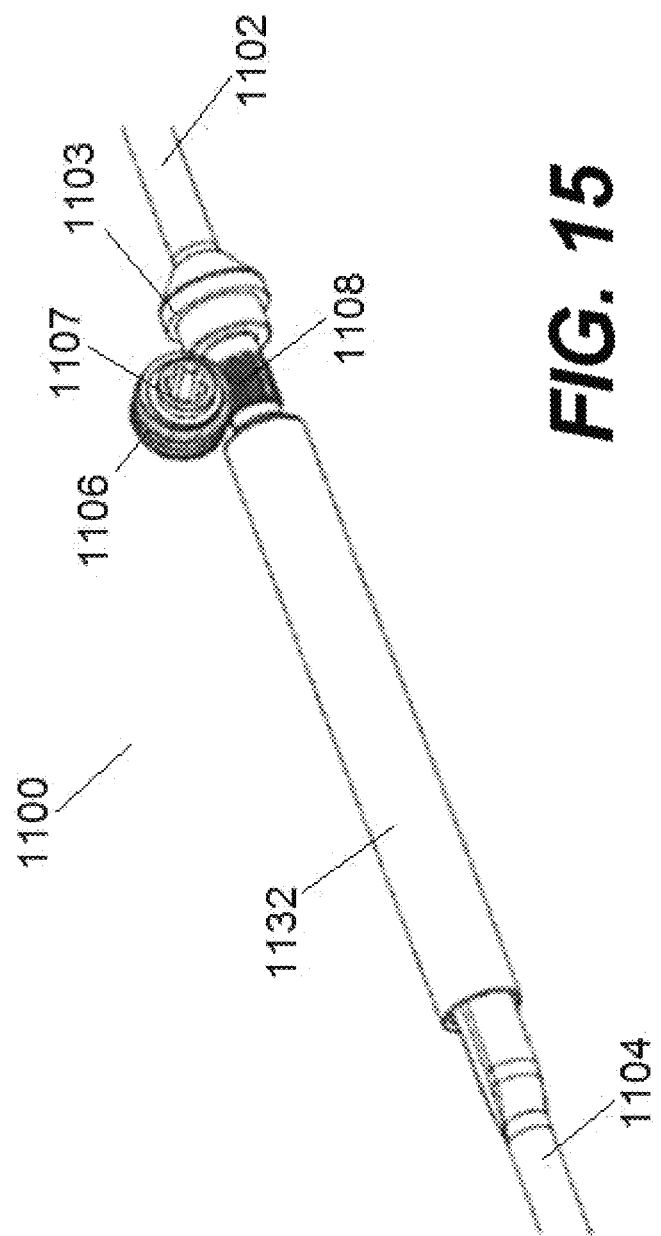
FIG. 15 is a top perspective view of the alternative growing rod of FIG. 14 with portions of the housing removed.

FIG. 15 is a top perspective view of the alternative growing rod of FIG. 14 with portions of the housing removed. In addition to the housing 1112, the cover plate 1142 has also been removed, thereby exposing the gear set 1106. From this view, one can see the inner threaded sleeve 1132 which threadingly engages the threaded portion of the extendible rod 1104. From this view, one can also see how rotation of the rotatable drive interface 1106 causes rotation of the worm gear 1108, which in turn causes rotation of the inner threaded sleeve 1132 and translation of the extendible rod 1104.

Figure 16:
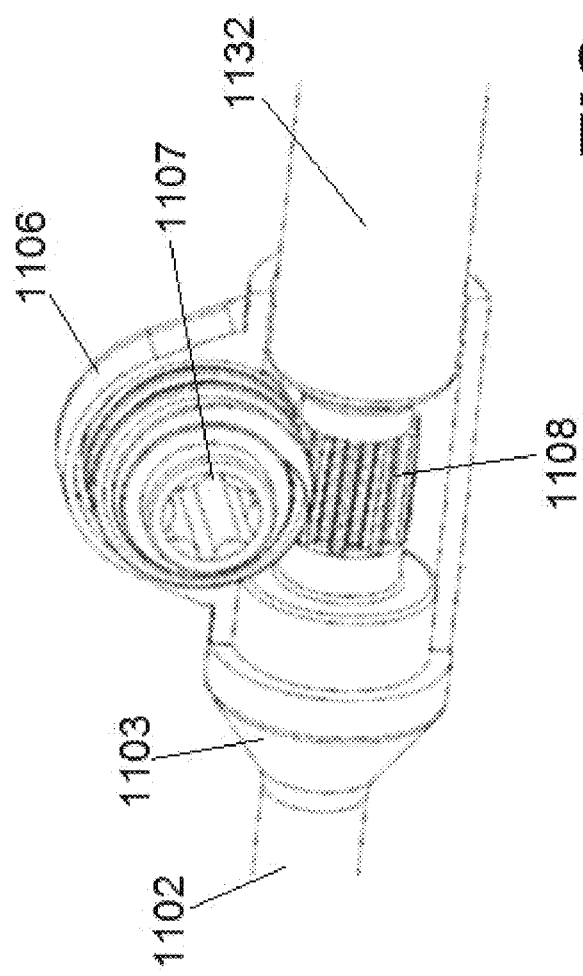
FIG. 16 is a close up view of the gear set of the alternative growing rod of FIG. 14.

FIG. 16 is a close up view of the gear set of the alternative growing rod of FIG. 14. The gear set 1106 comprises a worm gear set including a worm in the form of a rotatable drive interface 1106 and a worm gear 1108. As shown in this figure, the worm gear 1108 is attached to the inner threaded sleeve 1132 (e.g., via welding). As such, rotation of the worm gear 1108 causes rotation of the inner threaded sleeve 1132, which thereby causes linear translation of an extendible rod 1104 therein.

In some embodiments, the growing rod 1100 can incorporate a pre-lordosed housing 1112 and extendible rod 1104. Such a design can also incorporate a flexible inner threaded sleeve 1132. Advantageously, by providing a pre-lordosed growing rod 1100, this removes the flexural forces that can incur between the housing 1112 and extendible rod 1104, and can further allow for more beneficial contouring of the growing rod 1100 to a patient's anatomy.

In some embodiments, the growing rod 1100 can be affixed to a spine via one or more bone screws. The growing rod 1100 can be implanted in either up or down position and can be used singularly or in pairs. In some embodiments, the growing rod 1100 can be engaged through a small incision with a hexalobular drive interface. In some embodiments, the worm gear set 1106 provides a reduction ration of 6:1, 8:1, 10:1 or more. In some embodiments, the worm gear set 1106 provides a reduction ratio of 10:1 such that the rotatable drive interface 1107 is rotated 6 complete revolutions to achieve 1 mm of growing rod 1100 expansion or contraction, with the amount of growth based upon a goal measure of 1.8 cm to 2.4 cm per year. Advantageously, a surgeon can fine tune the amount of expansion by either increasing or decreasing the amount of rotations. If a surgeon feels too much distraction has been incorporated, the growing rod 1100 can be reduced by simply reversing the direction of the driver.

Advantageously, the growing rod 1100 and previous designs can be implanted via use of existing pedicle screws. In some embodiments, the growing rod 1100 will have the strength of a conventional rod, and can be adjusted via minimal incision. Per the worm gear set 1106, a controlled adjustment can be accomplished and distraction forces can be easily met. In some embodiments, the growing rod 1100 can be manufactured using a metal, such as steel, cobalt chrome, or titanium.

Figure 17:
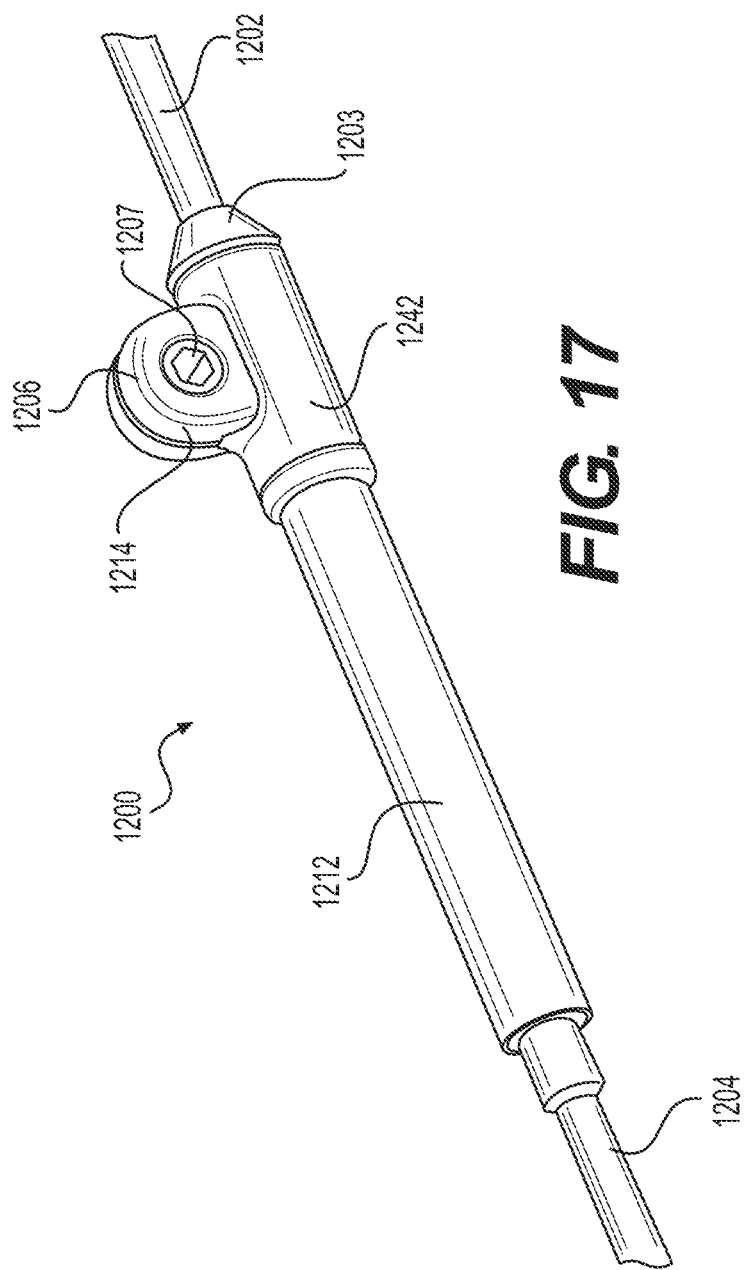
FIG. 17 is a top perspective view of another alternative growing rod in accordance with some embodiments.

FIG. 17 is a top perspective view of another alternative growing rod in accordance with some embodiments. The present growing rod 1200 includes a number of similar features to the growing rod 1100 in FIG. 14, including a fixed rod 1202, an extendible rod 1204, a housing 1212, a cover plate 1242, and a worm gear set 1206. In addition to these features, the growing rod 1200 includes an O-ring cover seal 1219 and a snubber, which will be discussed in more detail below.

The growing rod 1200 comprises a fixed rod 1202 and an extendible rod 1204. In some embodiments, the fixed rod 1202 is fixed relative to the housing 1212 and cover plate 1242, while the extendible rod 1204 is changeable in length relative to the housing 1212 and cover plate 1242. In some embodiments, the fixed rod 1202 comprises an end cap 1203 that is operably connected to the cover plate 1242.

Like the growing rod 1100, the cover plate 1242 of the growing rod 1200 covers a worm gear set 1206. The worm gear set 1206 comprises a rotatable drive interface 1207 that is accessible via a driver through an eyelid 1214 of the cover plate 1242. Rotation of the rotatable drive interface 1207 causes rotation of a worm 1209 (shown in FIG. 18). As the worm 1209 is attached to an inner threaded sleeve 1232 (shown in FIG. 18), it causes the inner threaded sleeve 1232 to rotate. As the extendible rod 1204 is attached to the inner threaded sleeve 1232 by a threaded engagement, it translates laterally, thereby causing expansion or contraction of the extendible rod 1204.

Figure 18:
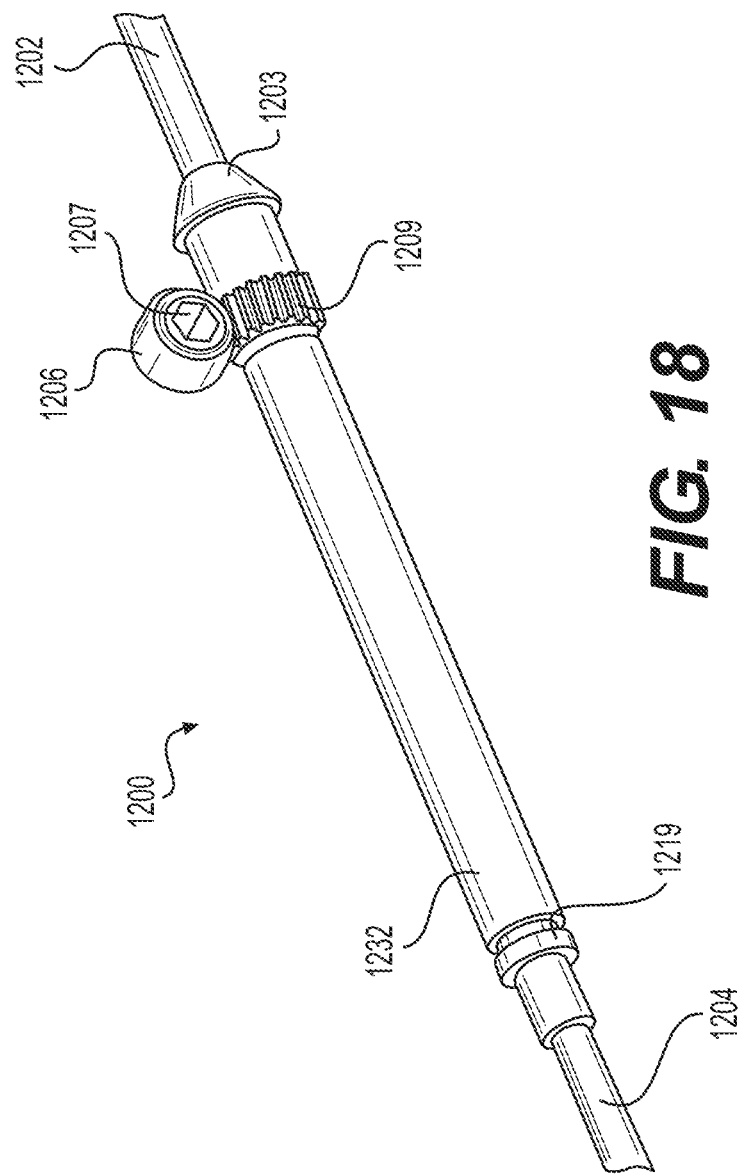
FIG. 18 is a top perspective view of the alternative growing rod of FIG. 17 with portions of the housing removed.

FIG. 18 is a top perspective view of the alternative growing rod of FIG. 17 with portions of the housing removed. From this view, one can see the O-ring cover seal 1219, which extends around the extendible rod 1204. The O-ring cover seal 1219 advantageously helps to seal the housing 1212 from the migration of blood or bodily fluids. In addition, the growing rod 1100 can include an optional snubber that helps to control any backlash from the gear set 1206.

Figure 19:
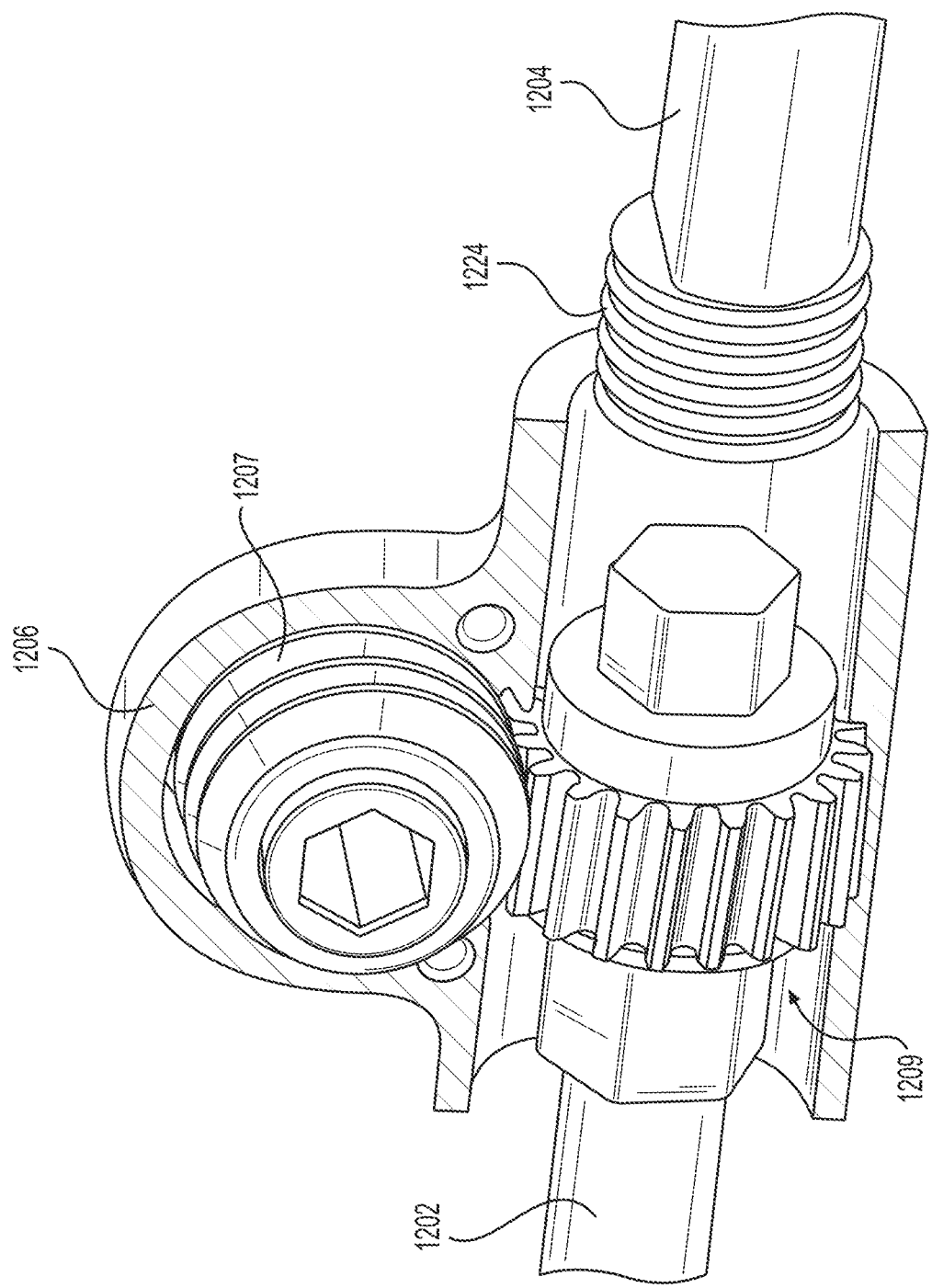
FIG. 19 is a close up view of the gear set of the alternative growing rod of FIG. 17.

FIG. 19 is a close up view of the gear set of the alternative growing rod of FIG. 17. From this view, one can see the worm gear set 1206 which includes the worm in the form of a rotatable drive interface 1207 and the worm gear 1209. In some embodiments, the worm gear 1209 can include a hex portion that is welded to the inner threaded sleeve 1232, which is not visible in FIG. 19. As the worm gear 1209 is attached to the inner threaded sleeve 1232, rotation of the worm gear 1209 causes the inner threaded sleeve 1232 to rotate, thereby causing translation of the extendible rod 1204.

In some embodiments, the growing rod 1200 can incorporate a pre-lordosed housing 1212 and extendible rod 1204. Such a design can also incorporate a flexible inner threaded sleeve 1232. Advantageously, by providing a pre-lordosed growing rod 1200, this removes the flexural forces that can incur between the housing 1212 and extendible rod 1204, and can further allow for more beneficial contouring of the growing rod 1200 to a patient's anatomy.

In some embodiments, the growing rod 1200 can be affixed to a spine via one or more bone screws. The growing rod 1200 can be implanted in either up or down position and can be used singularly or in pairs. In some embodiments, the growing rod 1200 can be engaged through a small incision with a hexalobular, or hex, drive interface. In some embodiments, the worm gear set 1206 provides a reduction ration of 6:1, 8:1, 10:1 or more. In some embodiments, the worm gear set 1206 provides a reduction ratio of 10:1 such that the rotatable drive interface 1207 is rotated 6 complete revolutions to achieve 1 mm of growing rod 1200 expansion or contraction, with the amount of growth based upon a goal measure of 1.8 cm to 2.4 cm per year. Advantageously, a surgeon can fine tune the amount of expansion by either increasing or decreasing the amount of rotations. If a surgeon feels too much distraction has been incorporated, the growing rod 1200 can be reduced by simply reversing the direction of the driver.

Figure 20:
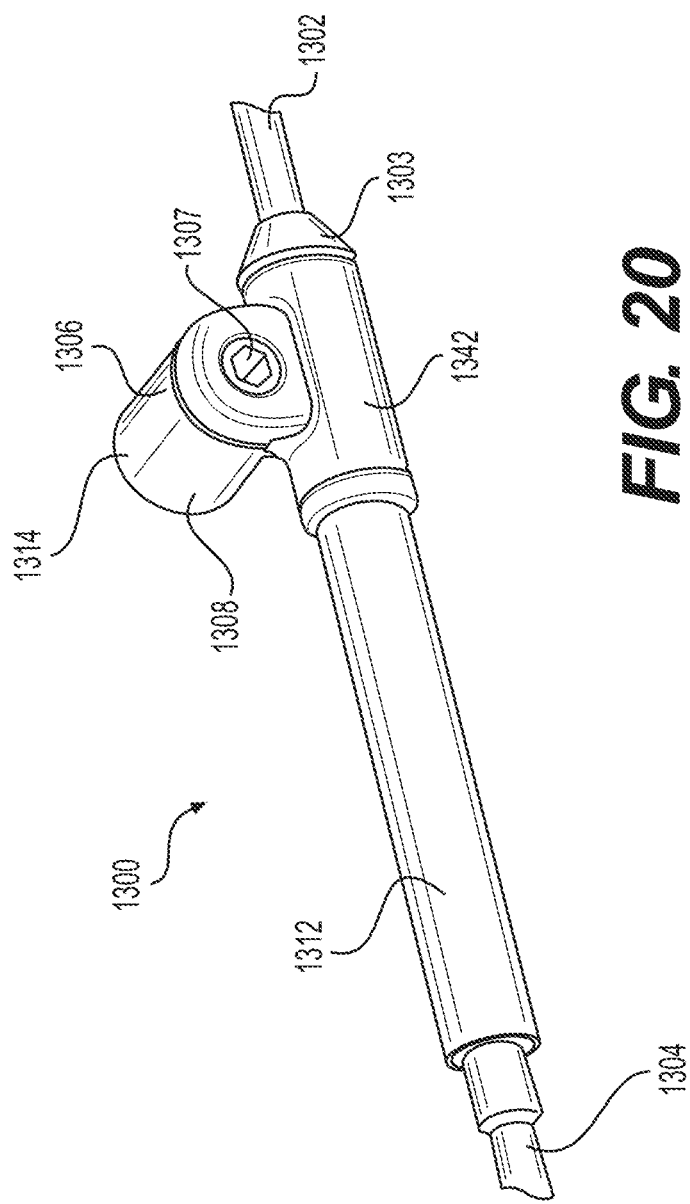
FIG. 20 is a top perspective view of a growing rod including a magnet in accordance with some embodiments.

FIG. 20 is a top perspective view of a growing rod including a magnet in accordance with some embodiments. The growing rod 1300 advantageously comprises a combined magnet and worm gear set 1306 that can extend the length of the growing rod either by an external magnet or via a small incision with a manual driver. The surgeon thus has the option to extend the growing rod via the magnet, manual driver or both options, depending on the needs of a particular patient. In addition to this advantage, the worm gear itself helps to prevent inadvertent rotation (e.g., reverse rotation) of the gear set, thereby providing a stable growing rod 1300. In some embodiments, the growing rod 1300 further includes a planetary reduction gear 1319. The advantage of providing the planetary reduction gear 1319 (shown close up in FIG. 23) is that it provides greater gear reduction per rotation.

The growing rod 1300 comprises a housing 1312 attached to a cover plate 1342. The growing rod 1300 further comprises an extendible rod 1304 extendible through the housing 1312 and a fixed rod 1302. The extendible rod 1304 is capable of extending relative to the housing 1312 and cover plate 1342, while the fixed rod 1302 is fixed relative to these two components. The cover plate 1342 encases the gear set 1306, which in the present case advantageously includes both a magnet 1308 and a worm gear with a rotatable drive interface 1307, as will be discussed in more detail below.

Figure 21:
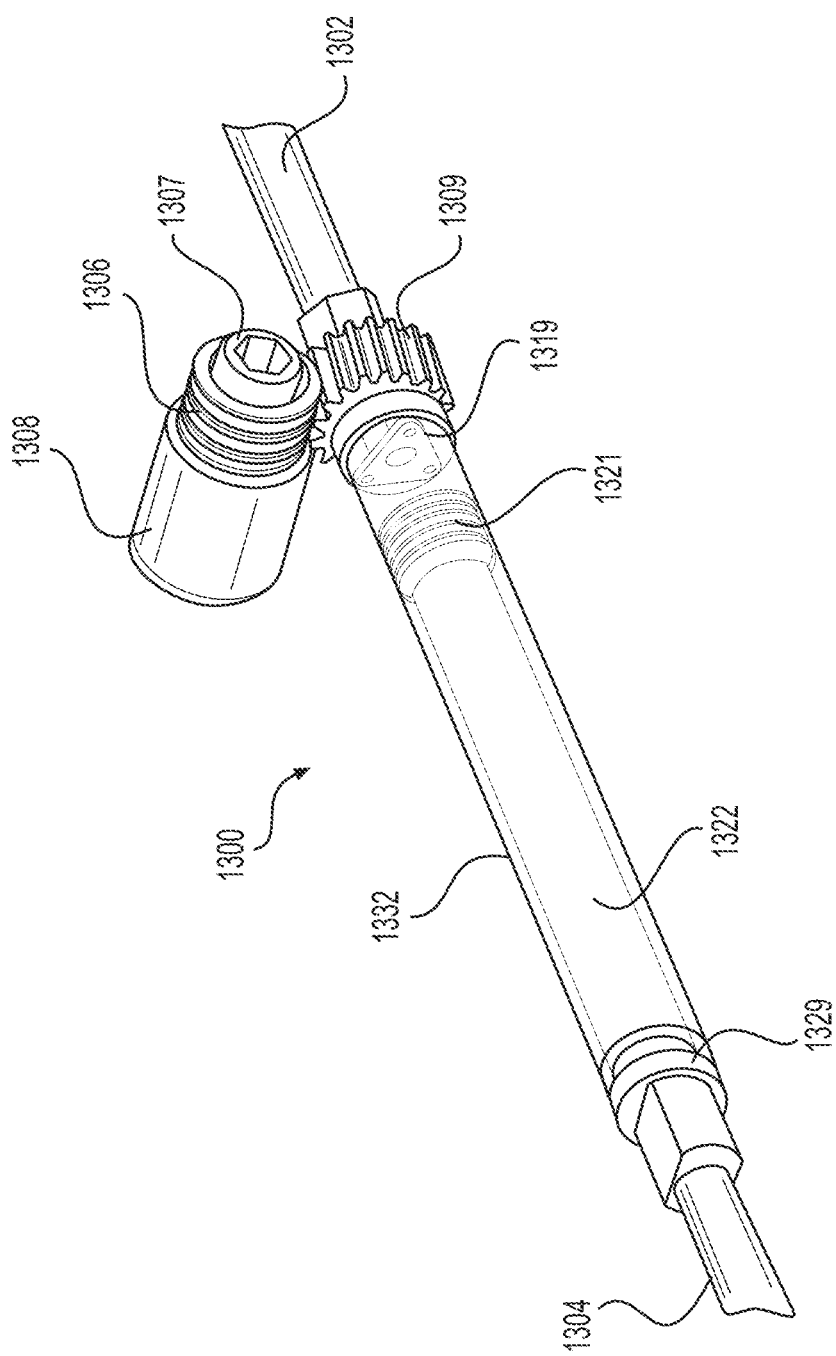
FIG. 21 is a top perspective of the growing rod of FIG. 20 with portions of the housing removed.

FIG. 21 is a top perspective of the growing rod of FIG. 20 with portions of the housing removed. From this view, one can see the inner threaded sleeve 1332 that is received in the housing 1312. In some embodiments, the inner threaded sleeve 1332 has a first end and a second end, wherein the first end is operably attached to the worm gear 1309. In some embodiments, the inner threaded sleeve 1332 is welded to the worm gear 1309. In addition, the inner threaded sleeve 1332 includes inner threads that engage with a threaded portion 1321 formed on the body 1322 of the extendible rod 1304. Advantageously, the worm gear 1307 can be rotated either magnetically or manually via a driver. Rotation of the worm gear 1307 causes the inner threaded sleeve 1332 (to which it is attached) to be rotated. As the extendible rod 1304 is threadingly engaged with the inner threaded sleeve 1332, the extendible rod 1304 will thus rotate and linearly translate, thus allowing the growing rod 1300 to extend in length. Rotation of the worm gear 1307 in an opposite direction causes the extendible rod 1304 to retract.

The gear set 1306 comprises a number of components including a magnet 1308, a worm including a rotatable drive interface 1307, a worm gear 1309 and a planetary gear 1319. The magnet 1308 is designed to extend radially from a longitudinal axis of the growing rod 1300. The magnet 1308 can be engaged via an external magnet that causes rotation of the magnet 1308 and worm 1307. By providing such a magnet, this advantageously provides a means for non-invasive growth of the growing rod 1300. The worm including the rotatable drive interface 1307 comprises an interface that can be engaged by an external driver (e.g., a hex driver). By providing such a rotatable drive interface 1307, this advantageously provides a means for minimally invasive growth of the growing rod 1300. As shown in FIG. 21, the magnet 1308 and the rotatable drive interface 1307 will rotate together, whether via magnet or manual driver. As these components rotate, the worm gear 1309 will also be rotated around the longitudinal axis of the growing rod 1300. As shown in FIG. 21, the worm gear 1309 can be operably attached to the planetary gear 1319. The planetary gear 1319 advantageously allows for greater expansion of the growing rod 1300 with less rotations of the worm gear 1309, thereby allowing the surgeon to expend less work during the procedure. In some embodiments, as shown in FIG. 21, a seal 1329 (e.g., an O-ring seal) can be received over the extendible rod 1304 to seal the housing 1312 from any migration of blood or bodily fluids.

Figure 22:
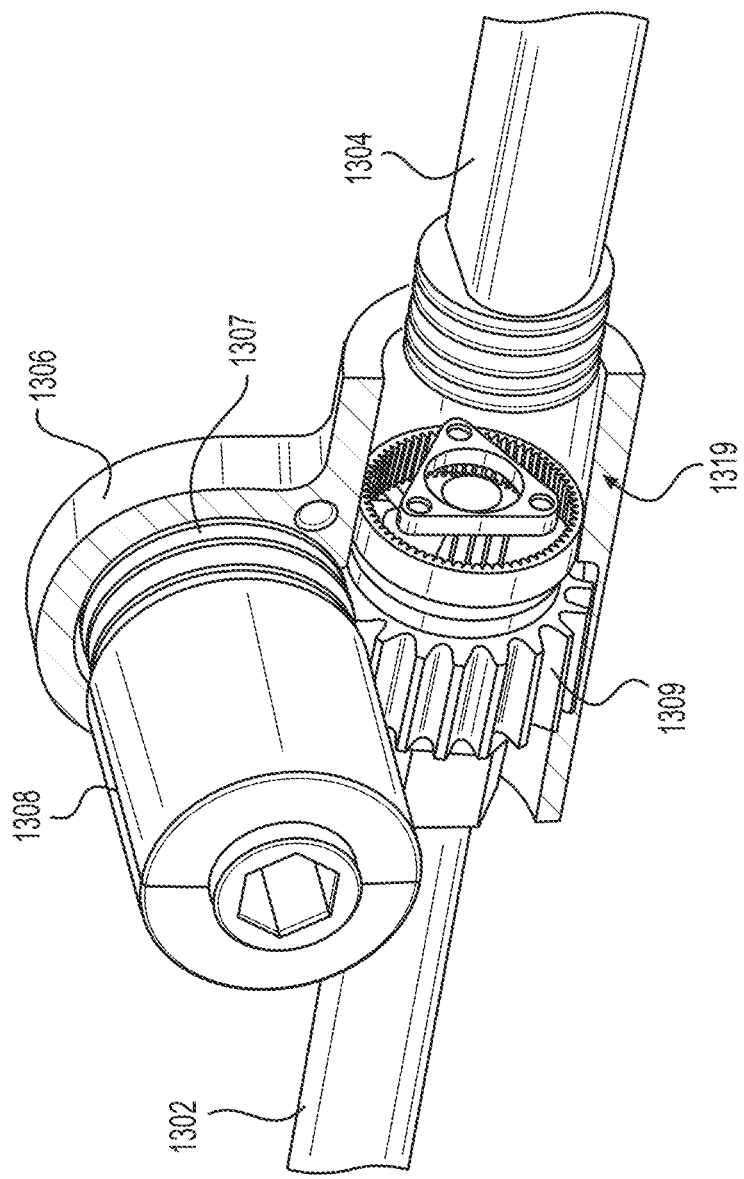
FIG. 22 is a close up view of the gear set of the growing rod of FIG. 19.

FIG. 22 is a close up view of the gear set of the growing rod of FIG. 19. From this view, one can see the magnet 1308, the cover plate eyelid 1306 housing the worm including the rotatable drive interface 1307, the worm gear 1309 and the planetary gear 1319. The worm gear 1309 and/or planetary gear 1319 can be attached to the inner threaded sleeve 1332 (not shown in FIG. 22), which is threadingly engaged with the extendible rod 1304.

Figure 23:
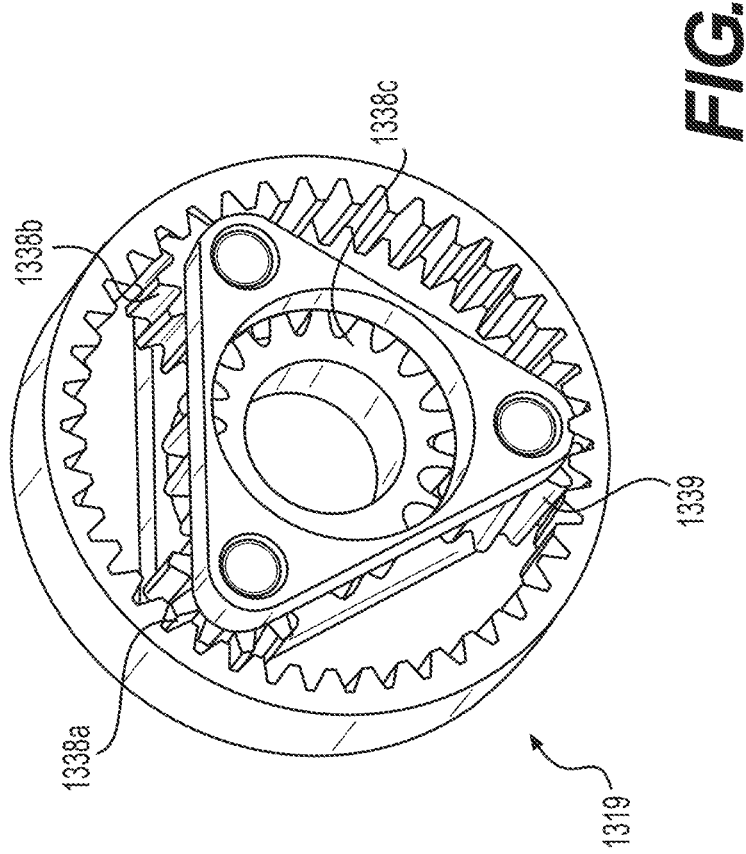
FIG. 23 is a close up view of a planetary gear of the growing rod of FIG. 19.

FIG. 23 is a close up view of a planetary gear of the growing rod of FIG. 19. The planetary gear 1319 comprises a gear hub 1339 engaged to a series of miniature gears 1338a, 1338b, 1338c. Rotation of the gear hub 1339 causes the miniature gears 1338a, 1338b, 1338c to rotate, thus causing the overall planetary gear 1319 to rotate.

In some embodiments, the growing rod 1300 can be implanted in either an up or down position and can be used singularly or in pairs. In some embodiments, the magnet 1308 and worm 1306 can be rotated 12, 14, 16, or 18 revolutions to achieve 1 mm of rod expansion or contraction, with the amount based upon a goal measure of 1.8 cm to 2.4 cm per year. The advantage of the growing rod 1300 is that it is designed to be implanted via use of bone screws (e.g., pedicle screws) as would a standard rod. The growing rod 1300 can be adjusted non-invasively with the magnet or via minimal incision. By providing a worm gear 1309 in conjunction with a planetary gear 1319, a controlled adjustment can be accomplished and distraction forces more easily met. In some embodiments, the growing rod 1300 can be made of a metal such as stainless steel, cobalt chrome, or titanium.

Referring now to FIGS. 24-32, a growing rod assembly 200 ("assembly 200") and its implantation into a spinal assembly will now be discussed. The assembly 200 provides a means for spinal lengthening for pediatric patients with early-onset idiopathic & neuromuscular scoliosis. The assembly 200 can provide precise distraction or contraction of the rod for multiple procedures over an extended period of years and can provide greater overall lengthening of rod than other systems. The assembly 200 can accommodate increments and forces to match the growth pattern in scoliosis patients, as well as provide a means of growth through either minimally invasive or external manipulation.

As used with assembly 200, the term "proximal" is defined as a direction toward the free end of the fixed rod 208 and the term "distal" is defined as a direction toward the free end of the expandable rod 220.

Referring to FIGS. 24-26 and 28, the assembly 200 includes a housing 202 in the form of a hollow sleeve. An expansion tube 204 with internal threads 205 is mounted in the housing 202 and extends the length thereof. In an exemplary embodiment, the threaded expansion tube 204 is constructed from a biocompatible titanium alloy.

A housing cap 206 is attached to and is part of the housing 202. A fixed rod 208 extends along a longitudinal axis 201 (shown in FIG. 28) proximally away from the housing 202, such that the housing cap 206 is located between the housing 202 and the fixed rod 208.

In an exemplary embodiment, the fixed rod 208 is constructed from a biocompatible titanium alloy or any other suitable biocompatible material. The fixed rod 208 has a distal end 254 (e.g., a conical distal end 254) that is fixedly connected to the housing cap 206, an elongate body 207 (e.g., a long 4.75 mm diameter cylindrical body 207), and a proximal end 209 (e.g., a pointed proximal tip 209). In an exemplary embodiment, the fixed rod 208 can be laser welded to the housing cap 206 or may be otherwise suitably connected or attached. The body 207 locks into any standard pedicle screw 60. For example, the body 207 may be combined with a pedicle screw 60 that accepts 4.75 mm diameter rods (see FIG. 32). The pointed proximal tip 209 allows the fixed rod 208 to tunnel through tissue when the rod 208 is being passed through the patient during implantation.

Figure 26:
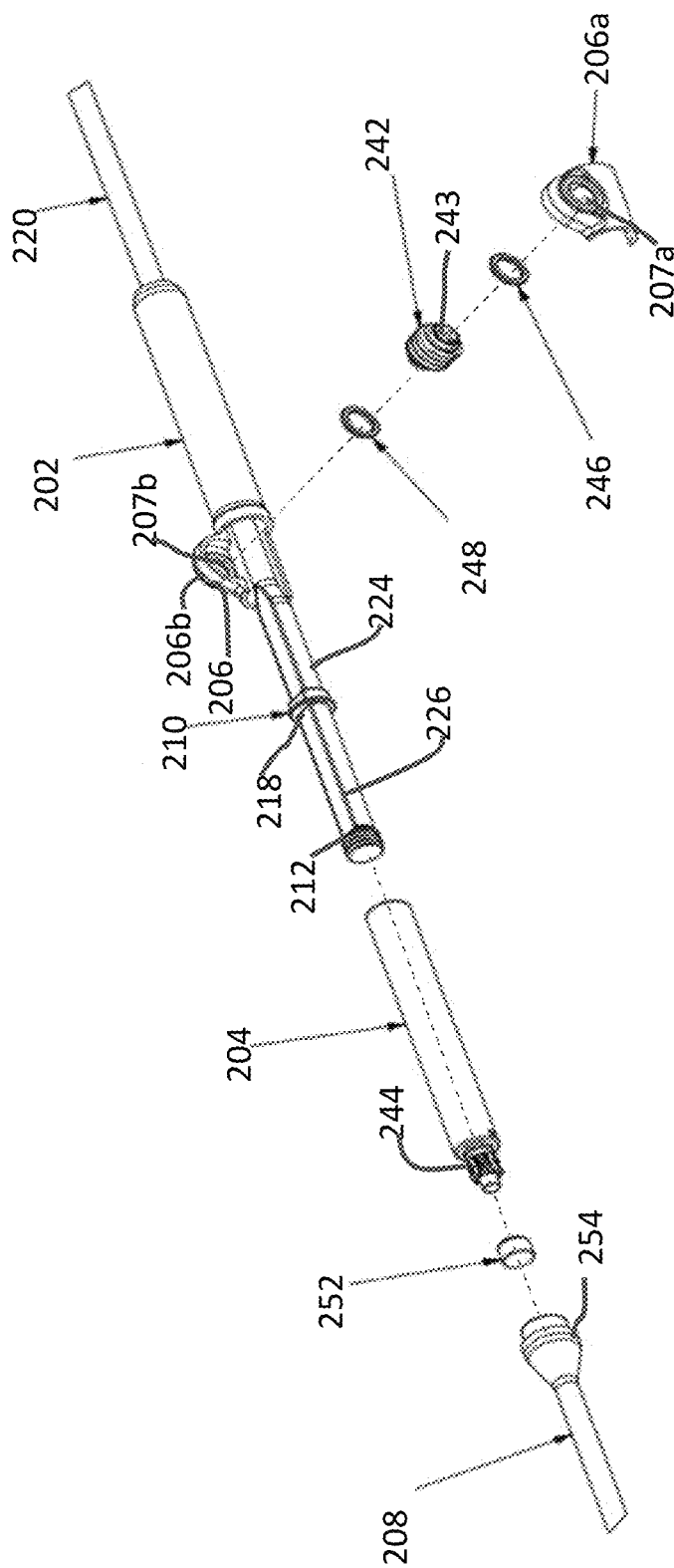
FIG. 26 is an exploded perspective view of the rod assembly of FIG. 24.
Figure 27:
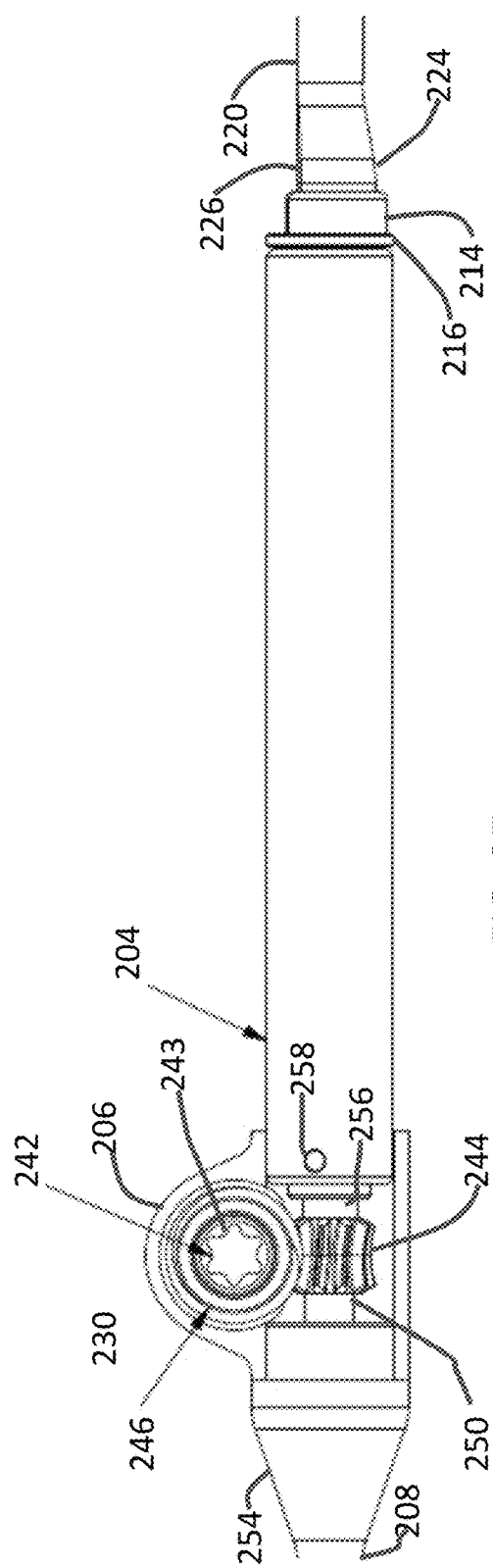
FIG. 27 is an enlarged side elevational view of the rod assembly of FIG. 24, with the housing omitted.

As shown in FIG. 26, the housing cap 206 includes first and second portions 206a, 206b that fit together with a worm drive 242 rotatably mounted between the portions 206a, 206b. In an exemplary embodiment, the housing 202 and the housing cap 206 are both made of biocompatible titanium alloy that are laser welded together to align and protect the internal components. It is contemplated, however, that suitable materials and modes of connection or attachment may be used. Each of the housing cap portions 206a, 206b has a through opening 207a, 207b, respectively, formed therein to allow access to either side of the worm drive 242.

Figure 28:
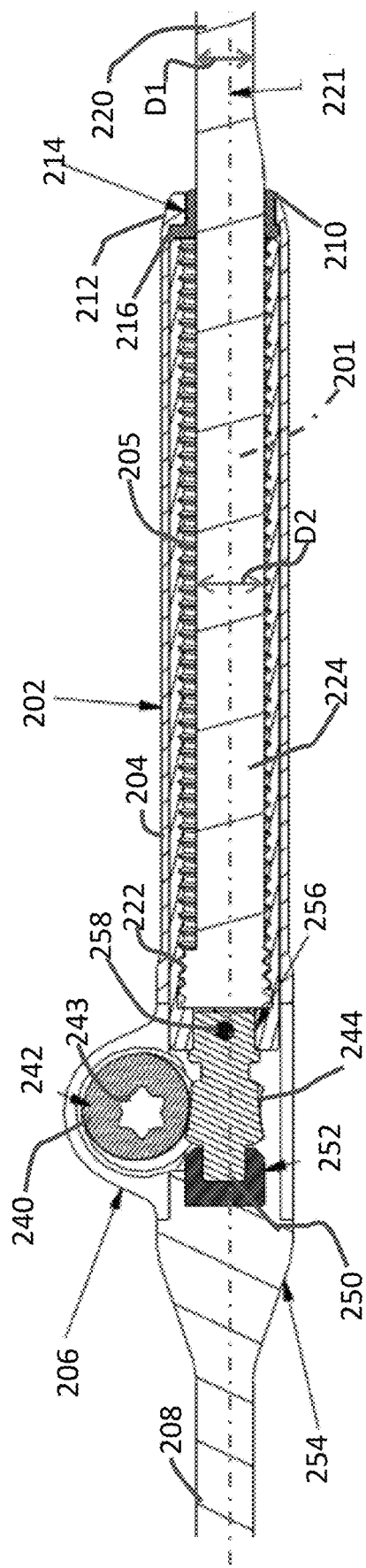
FIG. 28 is a side elevational view, in section, of the rod assembly of FIG. 24, with the extendible rod in a contracted position.

Referring to FIG. 28, a keyed bushing 210 is located in the housing 202 at a distal end 212 of the housing 202. The bushing 210 includes a central body portion 214 that is surrounded by a peripheral flange 216. A keyway 218 (shown in FIG. 26), for example, in the form of a flat surface is formed through the length of the bushing 210. In an exemplary embodiment, the bushing 210 can be constructed from biocompatible PEEK or other suitable materials and also functions to reduce friction and prevent wear between an expansion rod 220 and the housing 202.

The expansion rod 220 is extendible through and from the housing 202 along a longitudinal axis 201. A distal end portion 221 of the expansion rod 220 is adapted to extend outwardly from the distal end 212 of the housing 202. As shown in FIG. 28, the distal end portion 221 has a cylindrical cross-section diameter D1. In an exemplary embodiment, D1 is about 4.75 mm in order to accommodate commercially available pedicle screws that accept 4.75 mm diameter rods (see FIG. 32). Although it is contemplated that D1 may be of any suitable diameter to mate with a corresponding pedicle screw system. The distal end portion 221 is located outside the housing 202 and has a pointed tip 223 (shown in FIG. 25) that allows the tip 223 to tunnel through tissue when the expansion rod 220 is being passed through the patient during implantation.

Figure 29:
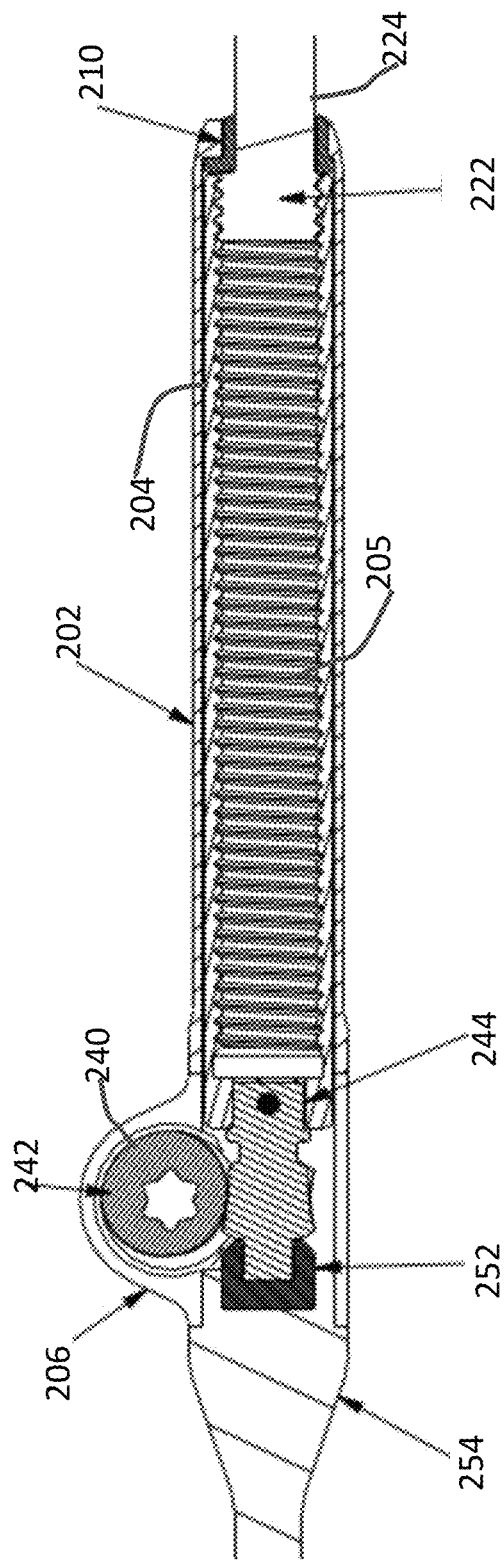
FIG. 29 is a side elevational view, in section, of the rod assembly of FIG. 24, with the extendible rod in an extended position.

The expansion rod 220 has a threaded proximal end portion 222 that is threadingly engaged with the threads 205 of the internally threaded expansion tube 204. The proximal end portion 222 has a larger diameter than the opening in the bushing 214 so that, when the expansion rod 220 is fully extended, as shown in FIG. 29, the bushing 214 retains the proximal end portion 222 in the housing 202.

A central body portion 224 extends between the proximal end portion 222 and the distal end portion 221. In a fully contracted position, as shown in FIG. 28, at least a portion of the central body portion 224 extends distally of the housing 202. The central body portion 224 has a diameter D2, larger than D1. The larger diameter D2 accommodates a mating key 226, for example, in the form of a flat surface (see FIG. 26) that engages the keyway 218 in the bushing 210 to prevent rotation of the expansion rod 220 as the expansion rod 220 extends out of or contracts into the housing 202. Therefore, as the internally threaded expansion tube 204 rotates, the threaded connection between the internally threaded expansion tube 204 and the threaded proximal end portion 222 of the expansion rod 220 causes the expansion rod 220 to translate longitudinally along the longitudinal axis 201.

Referring to FIG. 28, a driver assembly is disposed in the housing 202 and the housing cap 206 and is adapted to translate, or extend, the expansion rod 220 along the longitudinal axis 201 in a distal direction from the hollow housing 202.

In an exemplary embodiment, the driver assembly comprises a gear mechanism. Further, in an exemplary embodiment, the gear mechanism comprises a right-angle drive gear assembly. In an exemplary embodiment, the right-angle drive assembly comprises a worm gear assembly 240 having a worm drive 242 and a worm gear output 244 rotatable about the longitudinal axis 201. As shown in FIG. 28, the worm gear assembly 240 is located in the housing cap 206 between the housing 202 and the fixed rod 208.

The worm drive 242 is mounted in the housing cap 206 and is supported by worm bushings 246, 248 (shown in FIG. 26), such that one of the worm bushings 246, 248 is mounted on either side of the worm drive 242. In an exemplary embodiment, the worm bushings 246, 248 are constructed from biocompatible PEEK or other suitable material and are used to reduce friction and prevent wear when rotating the worm drive 242. In an exemplary embodiment, the worm drive 242 has a hexalobular drive interface 243 such that a corresponding Torx® wrench driver 70 (shown in FIG. 32) can be used to rotate the worm drive 242. It is contemplated that other suitable drive interfaces 243 and drivers 70 may be selected.

The worm gear output 244 has a proximal end 250 that is rotatably supported by an output gear bushing 252. The output gear bushing 252 is mounted in the distal end 254 of the fixed rod 208, as shown in FIG. 28. The output gear bushing 252 can be constructed from biocompatible PEEK or other suitable material. The gear bushing 252 serves to align the worm gear output 244 with the worm drive 242, reduce friction, and prevent wear between the gear output 244 and the fixed rod 208.

The worm gear output 244 has a distal end 256 that extends into and is fixedly connected to the internally threaded expansion tube 204, such as via a connecting pin 258. In an exemplary embodiment, the connecting pin 258 is constructed from a biocompatible titanium alloy or other suitable material. The expansion tube 204 is connected to the worm gear output 244 such that the expansion tube 204 rotates with the worm gear output 244, thereby translating the expansion rod 220 along the longitudinal axis 201 as the worm gear output 244 rotates, to extend or contract the expansion rod 220 from or into the housing 204 such that the assembly 200 expands or contracts in length, depending on the direction of rotation of the worm drive 242.

The worm gear assembly 240 allows a surgeon to turn the worm drive 242, which causes the expandable rod 220 to extend distally from the housing 202. In an exemplary embodiment, the worm drive 242 and the worm gear output 244 are both made of biocompatible cobalt chrome molybdenum alloy, and are designed with a pitch angle such that the worm drive 242 is able to drive the worm gear output 244, but not the reverse. Friction, as well as the pitch angle, between the worm drive 242 and the worm gear output 244 prevents the worm gear output 244 from rotating the worm drive 242. This feature is known as a self-locking feature and is useful to prevent the expansion rod 220 from expanding or contracting while under forces from the patient's spine without directly engaging the worm drive 242.

Figure 32:
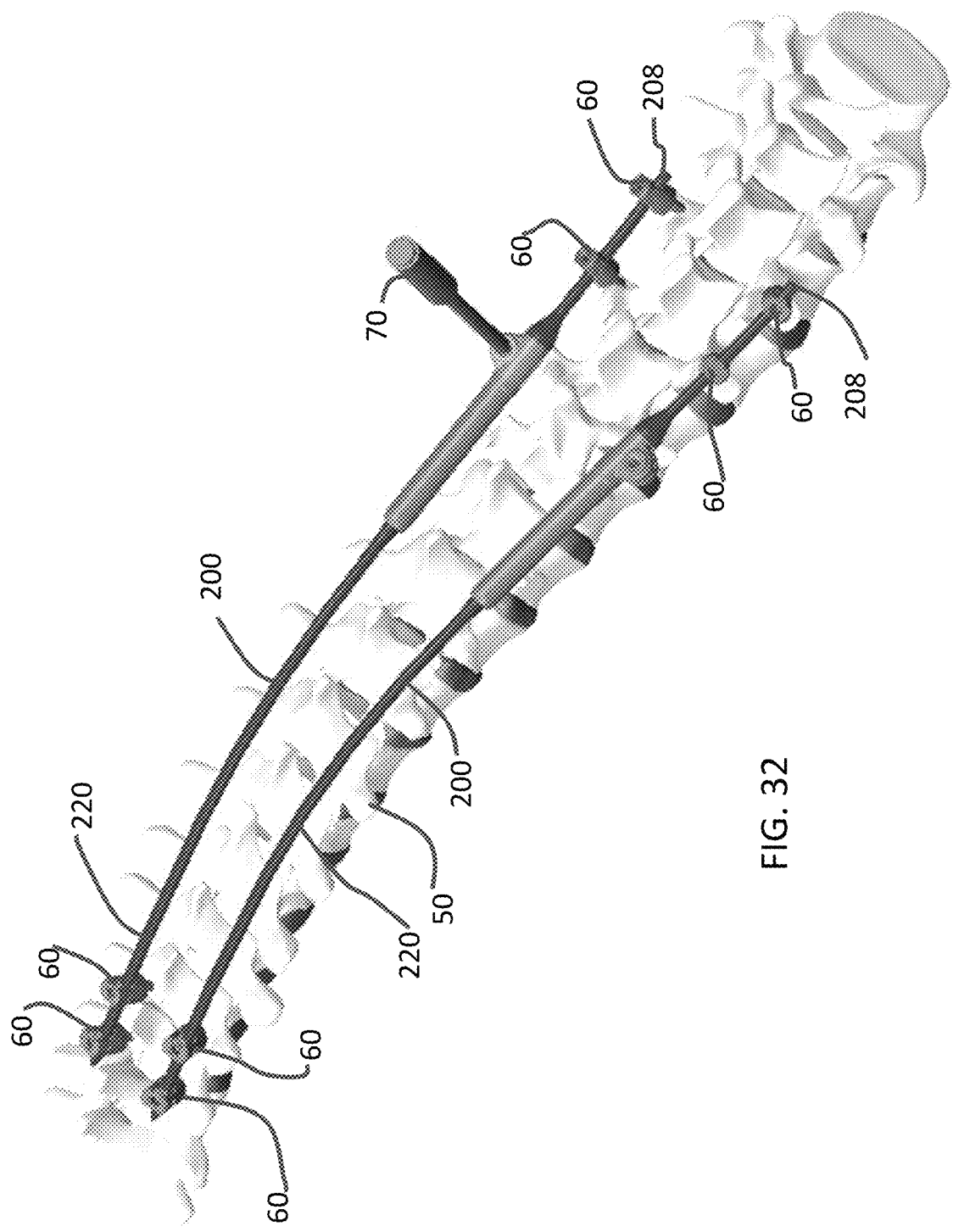
FIG. 32 is a lower perspective view of two rod assemblies of FIG. 24 implanted onto a patient's spinal column.

In some embodiments, as shown in FIG. 32, the assembly 200 can be affixed to a spine 50 via one or more pedicle screws 60. The pedicle screws 60 may be in the form of fasteners having a tulip or coupling body such as those described in U.S. Pat. No. 9,750,542, which is incorporated by reference herein. The assembly 200 can be implanted in either up or down position and can be used singularly or in pairs. In some embodiments, the assembly 200 can be engaged through a small incision with the drive interface 243 (e.g., hexalobular drive interface 243). In some embodiments, the worm gear assembly 240 provides a reduction ration of 6:1, 8:1, 10:1 or more. In some embodiments, the worm gear assembly 240 provides a reduction ratio of 10:1 such that for every 10 revolutions of the worm drive 242, the worm gear output 244 rotates one complete revolution. In an exemplary embodiment, the worm drive 242 is rotated about six (6) complete revolutions to achieve between about 1 mm and 1.25 mm of expansion or contraction of the expansion rod 220 from the housing 202, with the amount of growth based upon a goal measure of 1.8 cm to 2.4 cm per year. Advantageously, a surgeon can fine tune the amount of expansion by either increasing or decreasing the amount of rotations. This allows the surgeon to expand the expansion rod 220 against large forces caused by the deformity. If a surgeon feels too much distraction has been incorporated, the assembly 200 can be reduced by simply reversing the direction of the worm drive 242.

Advantageously, the assembly 200 can be implanted via use of existing pedicle screws 60. As shown in FIG. 32, two pedicle screws 60 are used at either end of the assembly 200 on the fixed rod 208 and the expansion rod 220 to secure the assembly 200 to a patient's spinal column 50. After implantation, the assembly 200 is engaged through a small incision via the drive interface 243 of the worm drive 242 with the specified driver 70.

Figure 30:
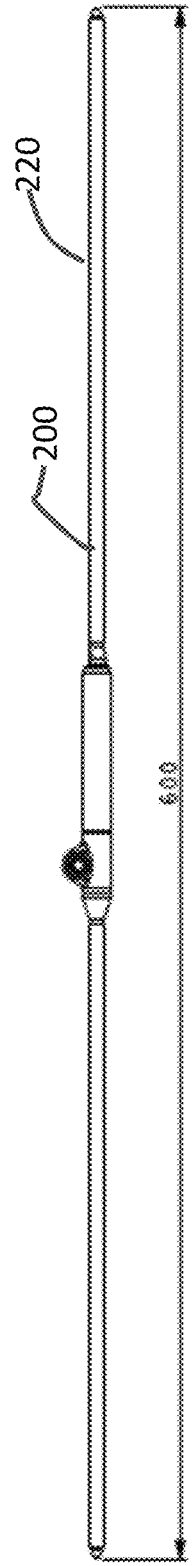
FIG. 30 is a side elevational view of the rod assembly of FIG. 24, showing an exemplary contracted length of the rod assembly.
Figure 31:
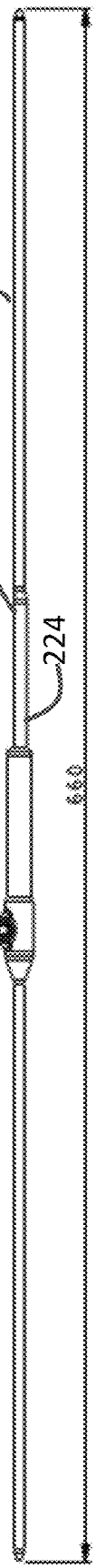
FIG. 31 is a side elevational view of the rod assembly of FIG. 24, showing an exemplary extended length of the rod assembly.

The assembly 200 can be implanted at any position along the spinal column 50 with the expansion rod 220 either caudal or cephalad and can be used singularly or in pairs (as shown in FIG. 32) depending on surgeon discretion. The length of the expansion rods 220 are oversized to allow the surgeon to cut, bend, and customize the expansion rod 220 depending on patient anatomy. The assembly 200 is designed to allow for an estimated minimum of 5 years of growth before replacement or removal is required. As shown in FIG. 30, in an exemplary embodiment, the assembly 200 is 600 mm long with the expansion rod 220 in a fully retracted position, and as shown in FIG. 31, in an exemplary embodiment, the assembly 200 is 660 mm long with the expansion rod 220 in a fully extended position, allowing for up to 60 mm of growth of the patient.

In some embodiments, the assembly 200 will have the strength of a conventional rod, and can be adjusted via minimal incision. By using the worm gear assembly 240, a controlled adjustment can be accomplished and distraction forces can be easily met. In some embodiments, the assembly 200 can be manufactured using a metal, such as steel, cobalt chrome, or titanium or other suitable biocompatible materials.

It is to be understood that the disclosure describes a few embodiments and that many variations of the invention can easily be devised by those skilled in the art. Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. An implantable growing rod assembly comprising:
a housing;
a fixed rod extending along a longitudinal axis away from the housing;
an expansion rod extendible from the housing along the longitudinal axis, the expansion rod having an exterior surface including a round portion that transitions in to a flat portion;
a keyed bushing having a length and located entirely within the housing, wherein the keyed bushing includes an interior round portion that transitions into an interior flat portion and an exterior round portion that transitions into an exterior flat portion, wherein the interior flat portion extends the entire length of the keyed bushing, wherein the interior flat portion mates with the flat portion of the expansion rod such that, as the expansion rod extends from the housing, the keyed bushing prevents the expansion rod from rotating; and
a driver assembly fixed to the housing and adapted to translate the expansion rod along the longitudinal axis, wherein a bushing is mounted in a distal end of the fixed rod.

2. The implantable growing rod assembly according to claim 1, wherein the housing comprises a hollow sleeve.

3. The implantable growing rod assembly according to claim 2, further comprising a threaded expansion tube mounted in the hollow sleeve.

4. The implantable growing rod assembly according to claim 3, wherein the expansion rod comprises a threaded proximal end threadingly engaged with the threaded expansion tube.

5. The implantable growing rod assembly according to claim 4, wherein the expansion rod comprises a distal end adapted to extend outwardly from the housing.

6. The implantable growing rod assembly according to claim 3, wherein the driver assembly comprises a gear mechanism.

7. The implantable growing rod assembly according to claim 6, wherein the gear mechanism comprises a right-angle drive gear assembly.

8. The implantable growing rod assembly according to claim 7, wherein the right-angle drive assembly comprises a worm gear assembly.

9. The implantable growing rod assembly according to claim 8, wherein the worm gear assembly comprises a worm gear output having a proximal end rotatably supported by the fixed rod.

10. The implantable growing rod assembly according to claim 8, wherein the worm gear assembly comprises a worm gear output having a distal end fixed to the threaded expansion tube such that the threaded expansion tube rotates with the worm gear output.

11. The implantable growing rod assembly according to claim 1, wherein the driver assembly is located in a housing cap between the housing and the fixed rod.

12. The implantable growing rod assembly according to claim 1, wherein the keyed bushing includes a keyway in the form of a flat surface formed through the length of the bushing.

13. An implantable growing rod assembly comprising:
a hollow housing made of a first material;
an expansion rod extendible from the housing along the longitudinal axis, the expansion rod having an exterior surface including a round portion that transitions in to a flat portion;
a keyed bushing having a length and made of a second material located within the housing, wherein the keyed bushing includes an interior round portion that transitions into an interior flat portion and an exterior round portion that transitions into an exterior flat portion, wherein the interior flat portion extends the entire length of the keyed bushing, wherein the interior flat portion mates with the flat portion of the expansion rod such that, as the expansion rod extends from the housing, the keyed bushing prevents the expansion rod from rotating;
a drive assembly connected to the housing and adapted to extend the expansion rod in a distal direction from the hollow housing; and
a fixed rod extending proximally from the hollow housing,
wherein the first material is different than the second material such that the second material is capable of reducing wear of the housing and the expansion rod,
wherein a bushing is mounted in a distal end of the fixed rod.

14. The implantable growing rod assembly according to claim 13, wherein the drive assembly comprises a gear assembly.

15. The implantable growing rod assembly according to claim 14, wherein the gear assembly comprises a worm gear assembly having a worm gear output rotatable about the longitudinal axis.

16. The implantable growing rod assembly according to claim 15, wherein the worm gear output is adapted to translate the expansion rod along the longitudinal axis.

17. The implantable growing rod assembly according to claim 15, wherein the worm gear output is connected to an internally threaded expansion tube disposed inside the hollow housing.

18. The implantable growing rod assembly according to claim 17, wherein the expansion rod comprises a threaded portion threadingly engaged with the internally threaded expansion tube.

19. The implantable growing rod assembly according to claim 18, wherein the threaded portion is located at a proximal end of the expansion rod.

20. An implantable rod assembly comprising:
a housing;
a housing cap attached to the housing;
a gear assembly located in the housing cap;
an expansion rod extendible from the housing along the longitudinal axis, the expansion rod having an exterior surface including a round portion that transitions in to a flat portion;
a keyed bushing having a length and located entirely within the housing, wherein the keyed bushing includes an interior round portion that transitions into an interior flat portion and an exterior round portion that transitions into an exterior flat portion, wherein the interior flat portion extends the entire length of the keyed bushing, wherein the interior flat portion mates with the flat portion of the expansion rod such that, as the expansion rod extends from the housing, the keyed bushing prevents the expansion rod from rotating; and
a fixed rod extending away from the housing along the longitudinal axis, wherein the gear assembly is adapted to extend the expansion rod such that the rod assembly expands in length, wherein a bushing is mounted in a distal end of the fixed rod.

\* \* \* \* \*